(12) United States Patent
Gorman

(10) Patent No.: US 10,792,142 B2
(45) Date of Patent: Oct. 6, 2020

(54) IMPLANTABLE AREAL DEVICE FOR SUPPORTING TISSUE

(71) Applicant: Joel Gorman, Kiryat Yearim (IL)

(72) Inventor: Joel Gorman, Kiryat Yearim (IL)

( * ) Notice: Subject to any disclaimer, the term of this patent is extended or adjusted under 35 U.S.C. 154(b) by 277 days.

(21) Appl. No.: 15/899,083

(22) Filed: Feb. 19, 2018

(65) Prior Publication Data

US 2018/0168791 A1 Jun. 21, 2018

Related U.S. Application Data

(63) Continuation-in-part of application No. 14/381,331, filed as application No. PCT/IL2013/000023 on Feb. 28, 2013, now abandoned.

(60) Provisional application No. 61/769,767, filed on Feb. 27, 2013, provisional application No. 61/603,958, filed on Feb. 28, 2012.

(51) Int. Cl.
*A61F 2/00* (2006.01)

(52) U.S. Cl.
CPC .... *A61F 2/0063* (2013.01); *A61F 2002/0068* (2013.01); *A61F 2250/0031* (2013.01); *A61F 2250/0067* (2013.01)

(58) Field of Classification Search
CPC ............ A61F 2/0063; A61F 2002/0068; A61F 2250/0031; A61F 2250/0067
See application file for complete search history.

(56) References Cited

U.S. PATENT DOCUMENTS

| | | | |
|---|---|---|---|
| 2003/0088149 A1* | 5/2003 | Raman ................. | A61F 2/2481 600/37 |
| 2004/0034373 A1* | 2/2004 | Schuldt-Hempe .... | A61F 2/0063 606/151 |
| 2011/0130774 A1* | 6/2011 | Criscuolo ............ | A61F 2/0063 606/151 |

* cited by examiner

*Primary Examiner* — Jocelin C Tanner

(57) ABSTRACT

An implantable areal device for supporting defective musculofascial tissue mechanically and by regeneration of muscle and fascial tissue. The device is formed by a plurality of thread sections that define a plurality of void spaces. At least one of the void spaces is more than one-hundred square millimeters in area. A method for supporting defective musculofacial tissue mechanically and by in-situ tissue engineering that includes the fixation of the device by open surgical techniques to defective musculofascial tissue. As a result, this fixation immediately provides mechanical support of the tissue, and subsequently provides physiological repair by allowing regenerative precursor cells to infiltrate freely into the void spaces and to proliferate therein, leading to regeneration of volumetric amounts of functionalized musculofascial tissue.

12 Claims, 24 Drawing Sheets

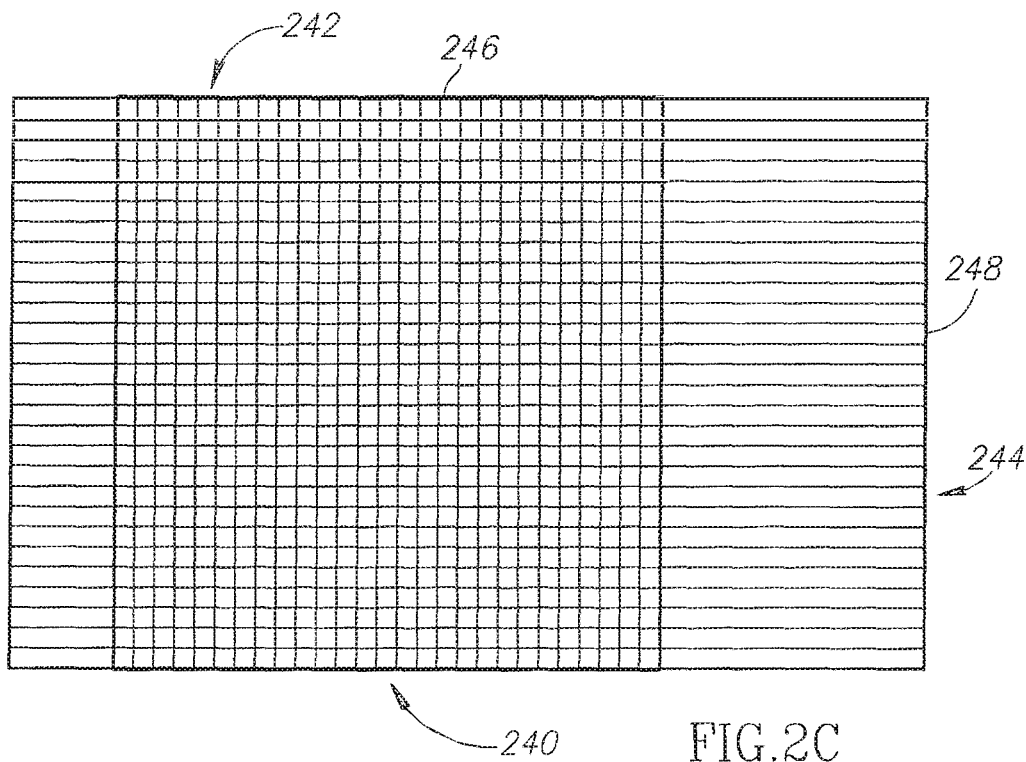
FIG.2C
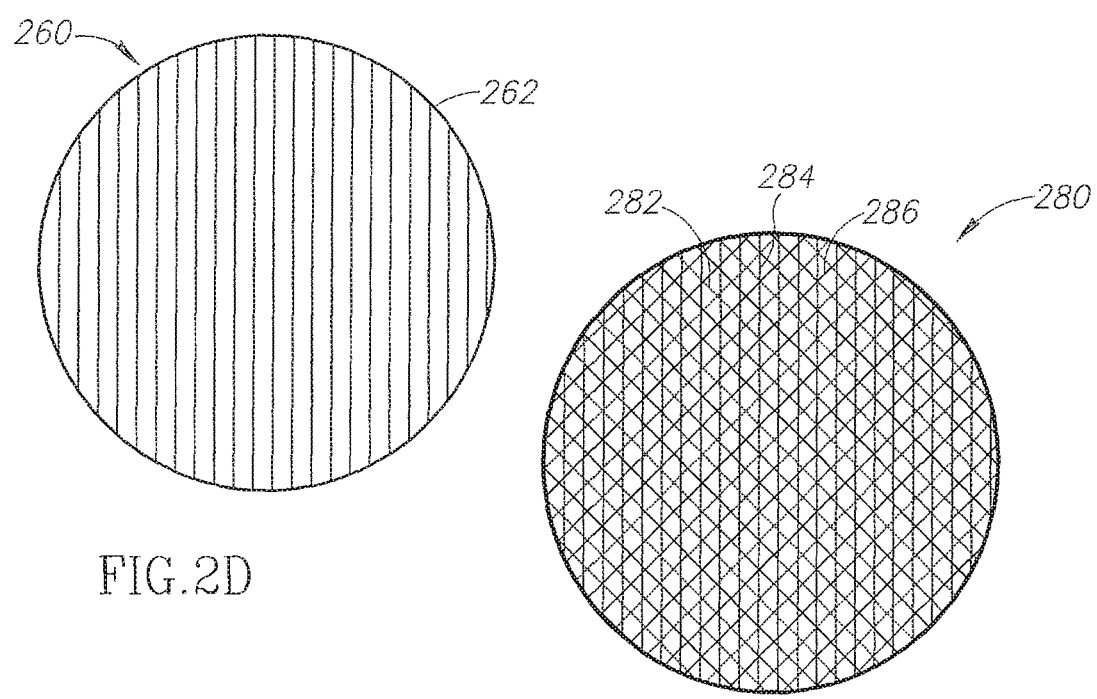
FIG.2D
FIG.2E

IMPLANTABLE AREAL DEVICE FOR SUPPORTING TISSUE

RELATED APPLICATIONS

This application is a continuation in part of U.S. patent application Ser. No. 14/381,331 filed on Aug. 27, 2014, which is a 371 of PCT/IL2013/000023 which claims benefit of 61/769,767 filed on Feb. 27, 2013 and of 61/603,958 filed on Feb. 28, 2012.

FIELD OF THE DISCLOSED TECHNIQUE

The disclosed technique relates to implantable devices in general, and to implantable devices for the surgical treatment of tissues, in particular.

BACKGROUND OF THE DISCLOSED TECHNIQUE

In general, a hernia is a protrusion of the internal content of a cavity through a defect in the wall of the cavity. The term "hernia" may also refer to the defect itself, through which the protrusion occurs.

Relevant Anatomy

In the field of human medicine, hernias most fre-quently occur in the abdomen, where intra-abdominal content protrudes out through a defect in the abdominal wall. This protruding content might include vital organs, usually parts of the intestine, or intra-abdominal fat, called "omentum". Since such protrusions are common and can lead to serious illness and death, the medical science of treating these protrusions receives ongoing attention and a surgical sub-specialty is entirely devoted to the treatment of Hernias of the abdominal wall.

The anterior wall of the human abdomen gets its strength and integrity primarily from three sheet-like muscles which are layered one on top of another and surround the front and sides of the abdomen. The muscle sheets are held together firmly by a facial envelope or "aponeurosis" that becomes notably thicker (approximately 1 mm), stronger and adherent to the muscles on the outer surface of this musculo-aponeurotic complex. External to the musculo-aponeurotic com-plex is the subcutaneous fat and overlaying skin of the abdo-men. Internal to this wall-like musculo-aponeurotic complex is the thin lining of the abdominal cavity called the "parietal peritoneum", which generally surrounds the enclosed inter-nal organs.

Causes of Hernias

Hernial defects occur in the musculo-aponeurotic layer of the abdominal wall either due to birth defects, the "wear and tear" of aging, or inadequately closed old surgical scars. When abdominal content protrudes out through the defect in the abdominal wall, the content is frequently cov-ered by the parietal peritoneum. This peritoneal covering thickens with time, presumably as a pathologic reaction to being out of place within the subcutaneous tissue. The thick-ened peritoneal covering gradually takes the form of a sac which grows larger as content therein progressively pro-trudes. This results in the characteristic bulging seen and felt as a hernia under the skin and fat.

Known Treatment of Hernias

Attempts to permanently correct hernias have been based on restoring the protruding contents back into the abdo-men and then surgically closing the defect in the abdominal wall through which the protrusion originally occurred. Since the defect is essentially a hole in the musculo-aponeurotic complex, all earlier attempts (from circa 1880 to 1980) to close the defect relied on the simple method of surgically sewing or "suturing" the defect with a needle and thread.

These suturing techniques however exhibited a high rate of reopening of the repair site and recurrence of the hernia. However, the rate of other complications (e.g., chronic pain, chronic infection) remained substantially limited.

More modern attempts of hernia surgery (circa 1960 to the present) were brought about by the post-World War II development of plastics, in the form of meshes, which are used to permanently close abdominal defects. In general, plastic meshes are either fiber-based networks or solid sheets. Known in the art fiber-based meshes are formed by weaving, interlacing, interweaving, knotting, knitting, winding, braid-ing, entangling or intertwining elongated elements, such as thread sections, which are intersected or substantially affixed with each other to form a network of nodes or intersections. These intersections are separated by holes, openings or pores, typically being evenly spaced. In known in the art fiber-based meshes, the individual plastic fibers are monofilaments, which are either closely intertwined or braided together. The highly braided or intertwined monofilament fibers are then further allied one to another in various patterns, such as matri-ces or random weaves. The overall result is a rough surface with numerous intersections, and numerous substantially small crevices or nooks-and-crannies at the macroscopic and microscopic levels. The applicant estimates the number of intersections per 100 square centimeters to be on the order of hundreds of thousands of intersections with the resulting crevices. The terms "fiber intersection" or "intersection" herein relate to two fiber sections firmly coupled with each other so as to prevent tissue growth there between. Unlike fiber-base meshes, most known in the art plastic solid sheet meshes exhibit micron-porosity, (i.e., the diameter of the pores is on the order of micrometers).

In general, plastic meshes are employed as implant-able permanent barriers or tissue reinforcing structures. The effective functioning of plastic meshes depends on the bio-compatibility (i.e., inertness) of plastic and on the permanent incorporability of the plastic mesh into the surrounding tis-sues. The term "incorporable" relates to the structure being able to be fully incorporated into the tissue. Regarding incor-porability, it is known in the art that an inflammatory tissue reaction is required for mesh incorporation to occur. In other words, for incorporation of the mesh into the tissue to occur, the mesh must stimulate the ingrowth of reactive tissue to attach to and surround the individual or groups of mesh fibers and thus fix the mesh permanently in place.

However, on a practical level, meshes have also introduced new mesh-related complications to hernia repair. These mesh related complications are, for example, chronic mesh pain, chronic mesh infection and significant visceral adhesions to the mesh. The relationship between the requirement of tissue reactivity for incorporability and mesh-related complications eventually became recognized. Generally, known in the art fiber-based meshes engender an inflammatory response other than the reaction required for tissue incor-poration alone. This inflammatory response may be a detri-mental side effect causing complications related to fiber-based meshes. Conversely, known in the art solid sheet meshes, which are non-reactive and do not allow for tissue attachment and ingrowth, are largely non-incorporable. This non-incorporability of solid sheet meshes causes the complications related to the solid sheet mesh.

The Detailed Causes of Complications of Current Mesh Surgery

OJ The drawbacks of current surgery of abdominal wall hernias using meshes are chronic mesh pain syndromes (e.g., foreign-body sensation, stiff-abdomen syndrome), chronic infection of the mesh, complications due to visceral adhe-sions to the mesh and hernia recurrence. Generally, the under-lying cause common to the complications of known in the art fiber-based meshes is the inflammatory reaction of the tissues to the intersecting fibers. As mentioned above, in known fiber-based meshes, monofilament threads are closely inter-twined or braided together and further allied one onto another. This results in a rough surface which includes a substantial number of nooks and crevices. These nooks and crevices cause the inflammatory response to proliferate and persist, which eventually results in the for-mation of primitive disor-ganized scar tissue. While the formation of such scar tissue may lead to the incorporation of the fiber-based mesh into the tissues, the scar tissue is also an uncontrolled foreign-body reaction, which may cause the mesh to stiffen and shrink by up to 40% of the mesh's original size. The stiffening of the mesh leads in turn to chronic mesh pain syndromes. The shrinkage of the mesh may cause the mesh to disattach from the tissues and migrate, leading to hernia recurrence. Moreover, the sub-stantial growth of inflammatory tissue engen-dered by the crevices encourages adhesion formation between viscera and the mesh, causing bowel obstruction and enterocutane-ous fistula. Also, the dense mass of the combined scar tissue and mesh may contribute to the sequestering of chronic infections.

The cause common to the complications of known in the art solid sheet meshes is the prevention of tissue ingrowth (i.e., either normal or inflammatory), which in turn prevents mesh incorporation. As a result the mesh is liable to migrate and cause hernia recurrence. Solid sheet meshes tend to become separated from the abdominal wall and walled-off or encapsulated, typical of a foreign body. This encourages chronic infections, which is characteristic of this type of mesh. In addition, the walled-off non-incorporated solid sheet acts as a permanent irritant causing significant chronic pain.

Known in the Art Methods to Decrease Mesh Complications

While the inflammatory or foreign-body reactions described above are essentially unavoidable following implantation of all known in the art fiber-based or solid sheet meshes, attempts have been made to cause the body to react differently to fiber-based meshes by manipulating either the placement position of the mesh or the material composition of the mesh.

Regarding placement position of the mesh, there are generally two known options. One option consists of exter-nal or "open" placement onto or into the abdominal wall via a large incision under direct vision. The other option consists of intra-abdominal placement via video-directed laparos-copy. With both options there are various ways for position-ing the mesh inside the body, each way exhibiting differing effects on the complications described above. The external option is less associated with intra-abdominal visceral adhe-sions, but more associated with chronic infections. Con-versely, laparoscopic placement increases the likelihood of complications from visceral adhesions but reduces the risk of mesh infection. Neither of these options substantially alters the high rate of chronic pain syndromes.

Regarding the options of placement positions using the external approach for minimizing complications, exter-nally placed meshes can be put in the following positions: "onlay", "inlay", "sublay" or "intraperitoneal". Onlay posi-tioning is considered simple to execute and substantially eliminates the risk of visceral adhesions. However a sub-stan-tially high rate of chronic infections is still observed. Inlay positioning consists of attaching the mesh to the borders of the hernia defect. Regardless of any advantages afforded thereby, the inlay position generally exhibits a high rate of hernia recurrence. Sublay positioning, which may be associ-ated with operative complications, reduces mesh infection and hernia recurrence, but stiff-abdomen and other chronic pain syndromes are not avoided. Intraperitoneal positioning also exhibits a high rate of visceral adhesions when using known in the art fiber-based meshes.

Regarding laparoscopic placement, two types of place-ments using known in the art meshes are common, namely total intra-abdominal placement and preperitoneal place-ment. With known in the art fiber-based meshes, the intra-abdominal placement exhibits a high degree of compli-cations, especially visceral adhesions and pain. Furthermore, intra-abdominal laparoscopic placed meshes are noted for being difficult to remove when necessary. Preperitoneal placement supposedly minimizes visceral adhesions and mesh infection, but does not minimize pain sequelae. In addi-tion, preperitoneal placement is considered a difficult surgical procedure to perform.

As mentioned above, altering the material compo-sition of fiber-based meshes has been attempted to reduce mesh-related complications. These attempts have been based on the recognition that the inflammatory response to fiber-based compositions is the direct cause of most of the compli-cations, as described above. Accordingly, attempts have been made to reduce the amount of inciting material in the mesh, for example, by using less material or by increasing the pore size between the braided or intertwined monofila-ment fibers. However, these material alterations still stimu-late the prolif-eration of the inflammatory tissue response when being incor-porated. Results from recent experiments using very large pore meshes of up to 3.6 millimeters pore diameter have not lowered complications significantly.

Alternative attempts have been made to control the inflammatory reaction by using non-synthetic biological materials, such as cross-linked or non-cross-linked acellular dermis of porcine or human origin. Biological meshes have a common property of being dissolved or absorbed by the inflammatory reactions of the tissues that they are meant to reinforce. As such, these biological meshes are generally precluded from the primary permanent treatment of abdomi-nal wall hernias. Nevertheless, they have two potential roles in abdominal wall surgery. First, when joined to a permanent synthetic mesh as a composite mesh, the biological mesh is meant to protect the synthetic mesh from visceral adhesions as the biological mesh gradually disappears. In practice how-ever, adhesions are still frequent and cause a high rate of complications. Furthermore, when the biological mesh is absorbed, the permanent synthetic mesh may still cause chronic pain syndromes. Secondly, biological meshes have proven very useful and often life-saving in "catastrophic" abdomen settings (e.g., a highly contaminated wide open abdomen), where permanent synthetic mesh is contraindi-cated due to the high probability of chronic mesh infection. A fully absorbed biological mesh may safely provide the necessary covering for the time period required for any potential source of contamination to resolve and for a definitive repair to be carried out. Unfortunately, the high cost of biological meshes is a major drawback in their use. In light of the above, it is apparent that the property which determines the effec-tiveness of known in the art meshes in repairing hernia defects, namely the reactivity of the mesh, is the same prop-erty that leads to mesh complications of current fiber-based and solid sheets meshes, namely infection, adhesions, pain and recurrence. Furthermore, the reactivity of biological meshes is the cause for absorption and eventual disappear-ance, leading to hernia recurrences.

U.S. Patent Application Publication No. 2009/0024147 to Ralph et al., entitled "Implantable Mesh for Mus-culoskeletal Trauma, Orthopedic Reconstruction And Soft Tissue Repair" is directed to implantable structures for the treatment of musculoskeletal trauma, orthopedic reconstruc-tion and soft tissue applications made of biocompatible mesh materials. The implantable structure of Ralph et al. includes two perpendicular sets of strands crossed over and under each other in an alternating pattern that intersects at points of contact. The spacing between the strands may be configured to produce a less permeable mesh with smaller voids or may be configured to tailor the voids (e.g., larger, smaller or vari-able spacing) according to hard or soft tissue ingrowth requirements. The strand material can be any biocompatible implant material such as metallic, bioresorbable polymers and non-resorbable polymers as well as organic materials such as collagen. The strands may exhibit various physical structures. For example, they can exhibit monofilament, thread or yarn structures. They can be braided or they can be hollow tubular structures and the hollow tubular structures can have a cross-section which is round, oval, square, rectan-gular, triangular or of any other closed geometric shape, including irregular shapes. When the hollow strands are either porous or biodegradable, the strands may be filled with medi-cation or bone growth substances to provide a timed release at the surgical site.

Publication number US20070282160 Sheu et al. (hereinafter "Publication 160") describes a mesh that contains non-degradable fibers with degradable fibers interspersed there between. The mesh of Publication 160 mesh is designed so that, as they degrade, the interspersed degradable fibers simultaneously are replaced by permanent and prominent scar tissue, so that any 'space' between these non-degradable fibers that is initially filled with the degradable fibers, later on is filled with newly formed scar tissue that in fact 'replaced' the degradable fibers as they degraded. Publication 160 depiction as to the diameter of pores/interstitial gaps therefore does not refer to the diameter of an actual space, but rather to a measurable distance between non-degradable fibers that is filled by prominent scar tissue. This distance, or "diameter", of "1 mm, or greater", referring to these scar-filled potential spaces, is neither comparable nor relevant to the diameter of actual open spaces of the implantable areal device according to the present invention, nor to a number of intersections surrounding and defining these open spaces.

Another important distinction exists between the mesh of Publication 160 and the implantable areal device according to the present invention on the basis of the latter's fundamental nature as a structure that supports tissue mechanically and by regeneration of functionalized musculofascial tissue. Whereas, in the disclosed technique the structure is designed to provide direct support to defective tissue, in Publication 160 direct support of the defective tissues of the urethra, sphincter muscles and pelvic floor is provided by prominent and permanent scar tissue formed by degrading fibers. The purpose of the non-degradable fibers remaining within the supportive scar tissue is to enhance the direct support provided by the flexible scar tissue, presumably by preventing over-flexibility. As such, the non-degradable part of the device described by Publication 160 is intended to provide secondary support to the directly supportive scar tissue, and is thus not comparable to the disclosed technique. In addition, the potential space between non-degradable fibers in the mesh of Publication 160 is described as equivalent to one millimeter square or greater, the intention of which being that they must be substantially smaller than one-hundred square millimeters in area, or otherwise the non-degradable fibers could not support effectively the scar tissue.

SUMMARY OF THE PRESENT DISCLOSED TECHNIQUE

The main object of the present invention is to provide an implantable areal device for supporting defective musculofascial tissue mechanically and by regeneration of muscle and fascial tissue. The implantable areal device is formed by a plurality of thread sections, wherein said thread sections define a plurality of void spaces. At least one of the void spaces is more than one-hundred square millimeters in area. It is also an object of the present invention to provide several methods, inter alia, a method for supporting defective musculofacial tissue mechanically and by in-situ tissue engineering. This method includes the following: (a) providing the implantable areal device, and (b) fixating by open surgical techniques the implantable areal device to defective musculofascial tissue, whereby the fixation immediately provides mechanical support of the tissue, and subsequently provides physiological repair by allowing regenerative precursor cells to infiltrate freely into the void spaces and to proliferate therein, leading to regeneration of volumetric amounts of functionalized musculofascial tissue.

It is also an object of the disclosed technique to provide a novel implantable tissue support structure for supporting tissue. In accordance with the disclosed technique, there is thus provided a tissue support structure which comprises a plurality of non-braided mono filament thread sections which define a surface. The tissue support structure induces substan-tially no foreign body reaction when supporting the tissue other than the reaction associated with the healing of tissue being in contact with a single non-braided monofilament thread and allows for substantially unimpeded ingrowth of healing tissue, by maintaining the number of mono filament thread intersections to be smaller than 10,000 intersections per one-hundred square centimeters. The thread intersection are defined as the crossing of two of the thread sections resulting from at least one of braiding, weaving, entangling, intertwining and affixing the thread sections.

BRIEF DESCRIPTION OF THE DRAWINGS

The disclosed technique will be understood and appreciated more fully from the following detailed descrip-tion taken in conjunction with the drawings in which:

FIGS. 2A-2F are schematic illustrations of parallel lines, implantable, incorporable and non-reactive tissue sup-port structures and tissue support structure arrays, with a stabilizing perimeter structure, constructed and operative in accordance with a further embodiment of the disclosed tech-nique;

DETAILED DESCRIPTION OF THE EMBODIMENTS

Figure 1A:
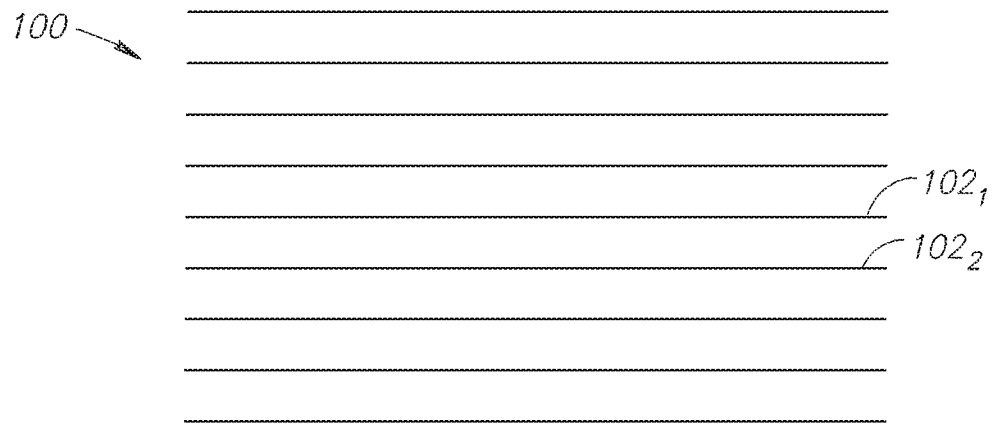
FIG. 1A is a schematic illustration of an implant-able, incorporable and non-reactive tissue support structure exhibiting the "parallel lines" configuration, constructed and operative in accordance with an embodiment of the disclosed technique.

The disclosed technique overcomes the disadvan-tages of the prior art by providing a tissue support structure for medical applications, for example, for the treatment of hernias of the abdominal wall. The tissue support structure according to the disclosed technique is an implantable, non-reactive and incorporable structure which is made of a singular non-braided monofilament thread or threads having between Zero and up to 10,000 thread intersections per 100 square centimeters (cm2). In other words, the tissue support structure according to the disclosed technique is made of singular non-braided monofilament thread sections which induce substantially no foreign body reaction other than the reaction associated with the healing of tissue being in contact with a single non-braided monofilament thread when sup-porting said tissue. Furthermore, the tissue support structure according to the disclosed technique allows for substantially unimpeded ingrowth of healing tissue (i.e., healing tissue which is associated with the healing of tissue being in contact with a single non-braided monofilament thread), by maintaining the number of monofilament thread intersections to be smaller than 10,000 intersections per 100 cm2.

A tissue support structure made of singular non-braided mono filament thread or threads may be stabilized by at least one stabilizing method or structure. The number of thread intersections per 100 cm2 is referred to herein as the "thread intersection density" or just the "intersection density". In addition the term "thread" and the term "fiber" are used herein interchangeably. The term "non-reactive" above relates to the fact that the tissue implanted with the tissue support structure of the disclosed technique does not exhibit a substantial foreign body reaction to the implanted structure other than the tissue reaction associated with healing tissue being in contact with a single non-braided monofilament thread. As mentioned above, the term "incorporable" relates to the ability of the structure to be fully incorporated into the tissue. Thus, the tissue support structure according to the disclosed technique is fully incorporable into the tissue, with-out causing substantial tissue reaction (i.e., being non-reactive).

As mentioned above, the tissue support structures accord-ing to the disclosed technique are constructed from a sin-gular non-braided monofilament thread or thread sections. In some embodiments, the thread sections do not intersect with each other (e.g., they are laid in parallel). In other embodi-ments of the disclosed technique, sections of the threads intersect with each other, thus creating a network. The tissue support structure may be stabilized, for example, by affixing the thread intersections at least at one point, by a stabilizing perimeter structure or by a central hub. The term "stabiliz-ing" herein refers to maintaining the structure or the thread sections relative to each other. Thus, the terms "stabi-lized" or "structurally stabilized" herein refer to the fact that the structure or the fiber sections relative to each other is maintained. The singular non-braided monofilament threads typically consist of nylon or other synthetic materials (e.g., metals, carbons and polytetrafluoroethylene). The threads may have a diameter of 0.2 mm or more. According to one embodiment the threads have a diameter of 0.35 mm. The threads may exhibit a circular cross-section, a rectangular cross-section or any other geometrical shape. Each thread may include protrusions (e.g., spherical bead-like bulges or cubical bulges), positioned intermittently along the thread at regular or irregular intervals there between. The size of each such protrusion may be up to one centimeter in diameter or as its longest side. Tissue support structures according to the disclosed technique may be coupled together, as further explained below, to create a tissue support structure array.

The tissue support structure according to the dis-closed technique may be used by applying the structure to hernia defects according to any of the methods of applying meshes, such as laparoscopically, or by non-laparoscopic open surgery using, for example, "onlay" or "sublay" posi-tioning, as explained above. The tissue support structure according to the disclosed technique is attached to the mus-culo-aponeurotic complex with, for example, sutures, clips or biocompatible adhesives.

Five configurations of the disclosed technique shall be exemplified herein below and described with reference to the figures. These five configurations are the parallel lines configuration, the matrix configuration, the randomly intersecting lines configuration, the radiating spokes with con-cen-tric rings configuration and the "quilted" hub and radiating spokes configuration. All of the described configurations are made of non-braided monofilament threads resulting in an implantable incorporable and non-reactive tissue support structure.

The "parallel lines" configuration is illustrated in FIGS. 1A-1C and 2A-2G. Reference is now made to FIG. 1A, which is a schematic illustration of an implantable, incor-porable and non-reactive tissue support structure exhibiting the "parallel lines" configuration, generally referenced 100, constructed and operative in accordance with an embodiment of the disclosed technique. Tissue support structure 100 includes parallel sections of singular, non-braided, mono filament threads, for example, threads 1021 and 1022. Thread 1021 and 1022 may be a #0 (i.e., 0.35 millimeters in diameter) monofilament nylon thread. It is noted that tissue support structure 100 requires a stabilizing perimeter struc-ture (not shown) as further explained below. The terms "stabilizing perimeter structure", "perimeter structure" and "frame" are herein used interchangeably. Stabilizing perimeter structures are further explained below.

Figure 1B:
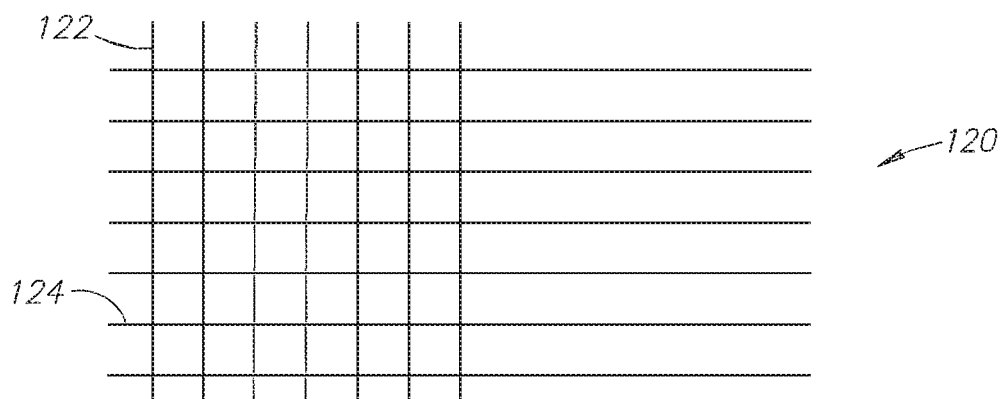
FIGS. 1B and 1C are schematic illustrations of implantable, incorporable and non-reactive tissue support arrays, constructed from tissue structures each exhibiting the "parallel lines" configuration in accordance with another embodiment of the disclosed technique.
Figure 1C:
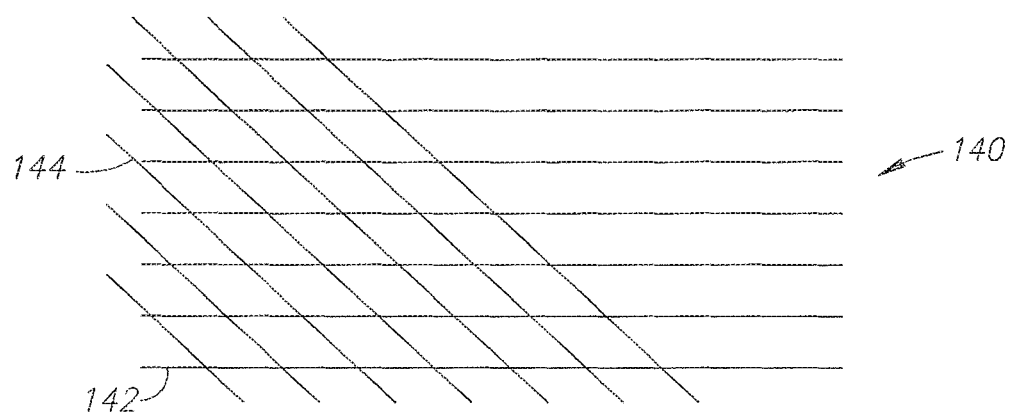
Figure 18:
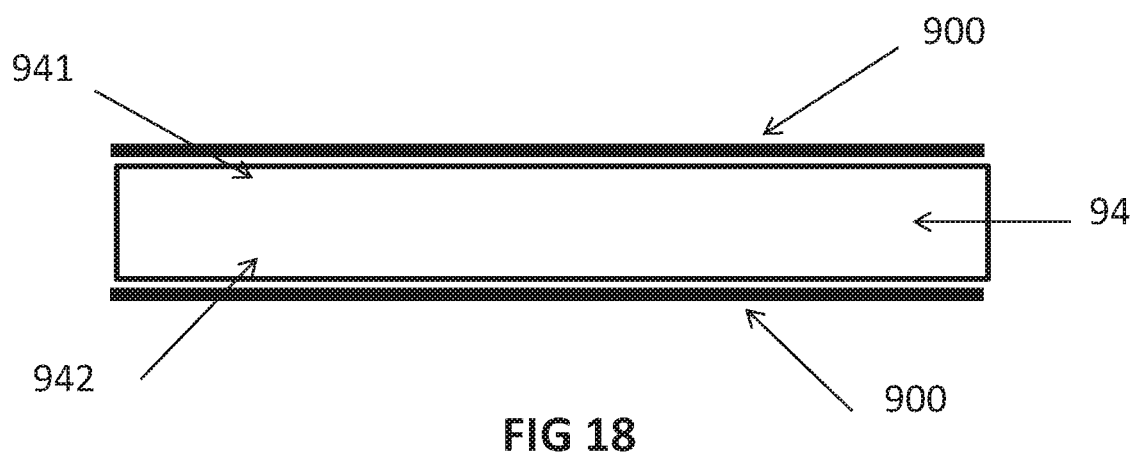
FIG. 18 illustrates schematically two implantable areal devices (900) that are placed as a sandwich on both sides (941) (942) of a tissue (94).

In general, a single layer of parallel threads depicted in FIG. 1A may serve as an implantable, incorporable and non-reactive tissue support structure. However, more than one layer placed one on top of the other at various angles may also be employed. Reference is now made to FIGS. 1B and 1C which are schematic illustrations of implantable, incorpo-rable and non-reactive tissue support arrays, generally referenced 120 and 140 respectively, constructed from tissue structures each exhibiting the "parallel lines" configu-ration of FIG. 1A, constructed and operative in accordance with another embodiment of the disclosed technique. In FIG. 18, a first layer 122 is laid over a second layer 124 such that the threads of the two layers are at right angles with respect to one another. In FIG. 1C, a first layer 142 is laid over a second layer 144 such that the threads of the two layers are at non-right angles with respect to one another. The distance between adjacent parallel lines (i.e., threads) may be, for example, 0.5 cm 1.0 cm, 2.0 cm or 3.0 cm.

Placing one layer on top of the other at various angles enables a surgeon to choose the required configuration (i.e., either a parallel lines configuration or an orderly intersecting configuration) according to real-time intra-operative considerations. It is noted that the non-layered parallel lines configuration provides a tissue support structure which con-tains a minimum of material and intersections (i.e., zero) per 100 cm2 of surface area.

Figure 2A:
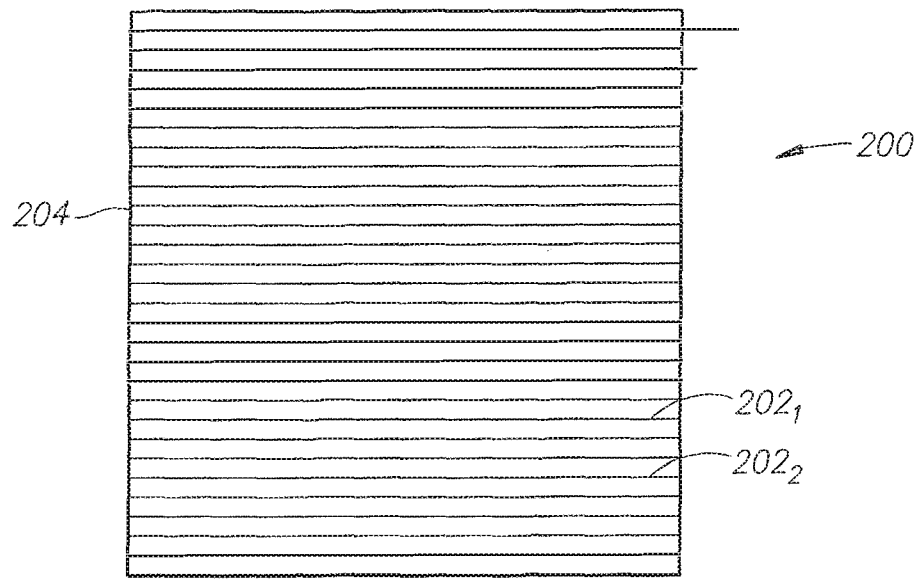
Figure 2B:
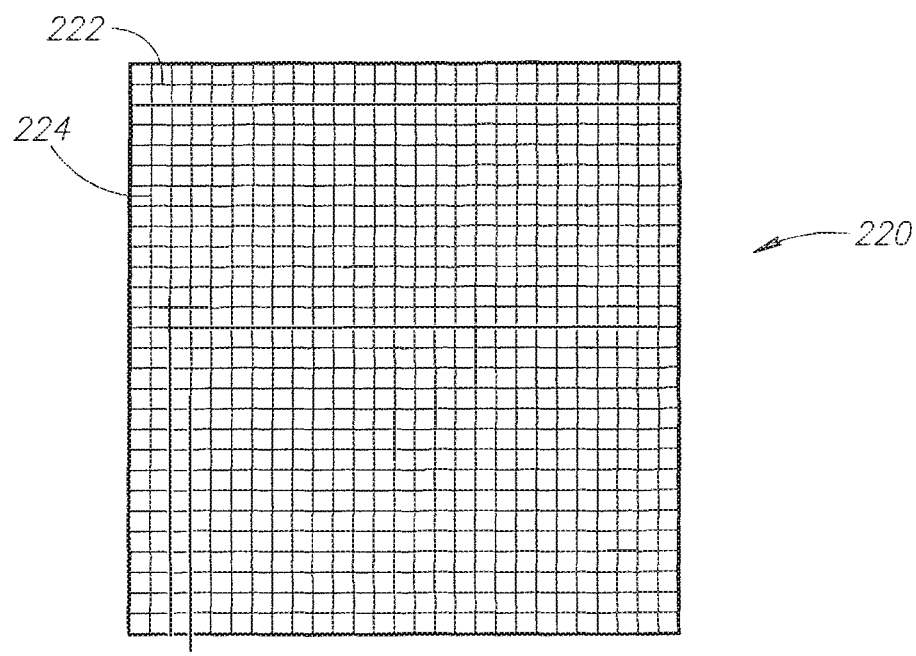

Tissue support structures exhibiting the parallel lines configuration may be stabilized with a stabilizing perimeter structure. Stabilizing perimeter structures are further explained below in FIGS. 9A-9B and 10. Parallel lines tissue support structures having such a stabilizing perimeter struc-ture are schematically illustrated in FIGS. 2A-2F. Reference is now made to FIGS. 2A-2F, which are schematic illustrations of parallel lines, implantable, incor-porable and non-reactive tissue support structures and tissue support structure arrays, with a stabilizing perimeter structure, generally referenced 200, 220, 240, 260, 280 and 300 respectively, constructed and operative in accordance with a further embodiment of the disclosed technique. In FIG. 2A, tissue support structure 200 includes a plurality of parallel singular mono filament threads such as threads 2021 and 2022, all connected at both ends to a stabilizing perimeter structure 204. Stabilizing perimeter structure 204 may be made of nylon, metals, carbon amalgams, silicon, polytetrafluoroeth-ylene (PTFE-also known commercially as Teflon®) or other inert materials.

a parallel lines tissue support structure array 220 with a stabilizing perimeter structure is made of two separate parallel lines structures, a first parallel lines structure 222 and a second parallel lines structure 224, each similar to tissue support structure 200 (FIG. 2A). Second structure 224 is laid on top of first structure 222 such that the parallel threads of first structure 222 are at a right angle with respect to the parallel threads second structure 224. Structure 222 has "vertical" parallel lines and structure 224 has "horizon-tal" parallel lines resulting in a matrix-like tissue support struc-ture array. The combined stabilizing perimeter struc-ture of tissue support structure 220 is composed of the respective stabilizing perimeter structures of tissue support structure 222 and of tissue support structure 224 coupled together. The coupling of different stabilizing perimeter structures is fur-ther explained below in conjunction with FIGS. 13A-13G.

The two or more overlaying structures do not nec-essarily exhibit identical shapes and sizes. For example, as depicted in FIG. 2C, a parallel line tissue support structure array 240 is made of two separate parallel lines structures, a first parallel lines structure 242 and a second parallel lines structure 244, each similar to tissue support structure 200 (FIG. 2A). First parallel lines structure 242 is laid over second parallel lines structure 244. First parallel lines struc-ture 242 includes a square stabilizing perimeter structure 246 and sec-ond parallel lines structure 244 includes a rectangular stabilizing perimeter structure 248. First parallel lines structure 242 may exhibit the dimensions of, for example, 10×20 cm or 20×30 cm. Second parallel lines structure 244 may exhibit the dimensions of, for example, 10×10 cm or 20×20 cm.

FIG. 2D depicts a parallel lines tissue support struc-ture 260 with a circular, ring shaped, stabilizing perimeter struc-ture 262. In FIG. 2E, tissue support structure array 280 is made of three circular structures 282, 284 and 286, each similar to tissue support structure 260 (FIG. 2D). The three circular structures 282, 284 and 286 are laid one on top of another such that the angles between the parallel threads of each of tissue support structure 282, 284 and 286 are non-right angles (e.g., 30 degrees, 60 degrees and the like).

In general, any number of layers may be placed at any appropriate angle with respect to one another, to create during surgery a multi-layered implantable, incorporable and non-reactive tissue support structure array. As mentioned above, when only one tissue support structure which exhibits the parallel lines configuration is used the intersection density is at a minimum (i.e., zero per 100 cm2).

The shape of a parallel lines tissue support structure, as defined by the stabilizing perimeter structure thereof, is related to the intended use of the tissue support structure. For example, when the intended purpose is to reinforce a large area of the abdominal wall (i.e., placed over an already mended defect in the abdominal wall), a rectangular shaped parallel lines tissue support structure may be used. Such a rectangular shape parallel lines tissue support structure will extend across the abdominal wall with the minimum number of intersections (i.e., zero per 100 cm2) thus rendering the tissue support structure non-reactive. When the intended use is to re-establish the barrier function of the abdominal wall (i.e., to actually bridge and thus mend a defect in the abdomi-nal wall), two or more parallel line tissue support structures may be overlaid one on top of the other, as explained above with reference to FIGS. 2C and 2E.

The circular parallel lines tissue support structure further extends the options of building a tissue support struc-ture during surgery. This is achieved by overlaying more than one identical circular structure, attached at their perimeters. A circular tissue support structure may come in various sizes. Examples of possible sizes include structures with a diameter of 5, 10, 15 or 25 cm.

Figure 2F:
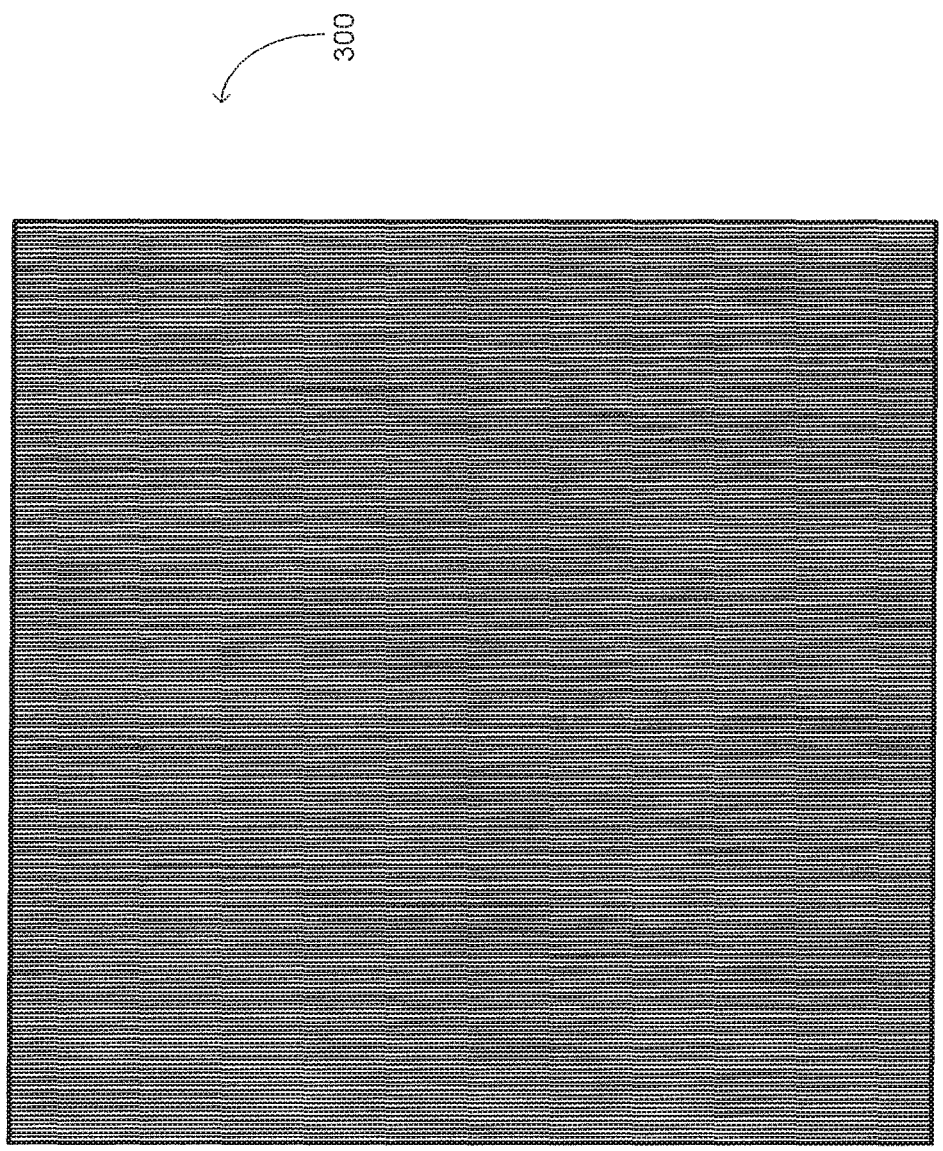

With reference to FIG. 2F, tissue support structure 300 is similar to a parallel line tissue support structure (e.g., tissue support structure 200 in FIG. 2A) with a stabilizing perimeter structure. The threads in tissue support structure 300 are non-braided monofilament threads, each exhibiting a diameter of at least 10 micrometers (i.e., the diameter of the threads is not necessarily uniform) and are placed in parallel one with respect to the other. Each thread may be in loose parallel contact with the threads adjacent thereto (i.e., adjacent parallel threads are in contact with each other but are not affixed to each other). Thus, tissue support structure 300 may exhibit similar characteristics to that of a solid surface. Alter-natively, adjacent pairs of threads may exhibit an intervening space there between. In yet another alternative, a first portion of the threads are in loose parallel contact with each other and a second portion of the threads exhibit an intervening space there between.

The tissue support structure 300 may be constructed with predefined tautness of the threads. Thus, a tradeoff between compliance of the threads sections to tissue ingrowth and the barrier and re-enforcement function of tissue support structure 300 is achieved. Additionally, tissue support structure 300 may be constructed with each thread section exhib-iting a respective tension. Nevertheless, even when adjacent threads are in contact with each other, the threads may be separated when opposing physiological forces are applied to the adjacent threads in the lateral direction. In this way, tissue support structure 300 allows unimpeded tissue ingrowth (i.e., since the thread sections shall move as the healing tissue grows), such as occurs in normal healing, between the threads. Thus, tissue support structure 300 is fully incorporable. Tissue support structure 300 simultane-ously exhibits characteristics of a non-reactive solid sheet (i.e., due to the use of singular non-braided monofilament threads with zero intersection density) and a fully incorpo-rable tissue support structure (i.e., due to the loose contact between the thread sections). Such a tissue support structure may by layered upon identical or other tissue support structure described herein. In FIG. 2F, tissue support struc-ture 300 exhibits the shape of a square. However, tissue support structure may exhibit various other shapes such as a rectangular, a circle or an ellipse. The size of tissue support structure 300 may exhibit various sizes (e.g., 2 cm or 30 cm as its longest side or diameter).

In the parallel lines configuration, the end parallel threads may be attached to stabilizing parallel rods, which are perpendicular to the threads. A surgeon can control these stabilizing parallel rods with regards to the tautness of the threads (e.g., by holding the two rods apart thus creating the desired tautness). Such a tissue support structure may be used in a similar way to any of the parallel lines configu-ration described above (e.g., being rolled for insertion via a laparo-scope).

Figure 2G:
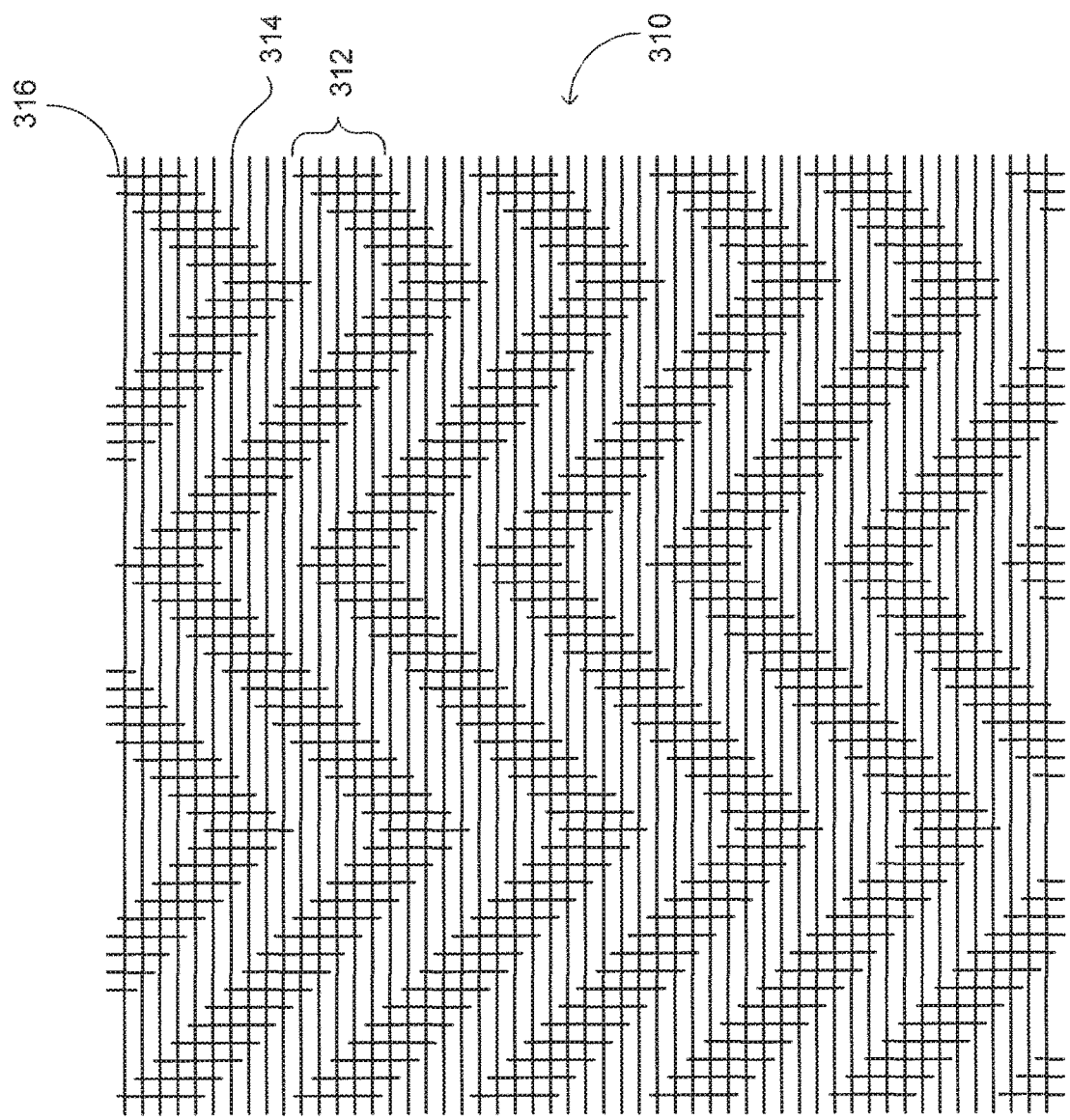
FIG. 2G is a schematic illustration of a tissue sup-port structure constructed and operative in accordance with another embodiment of the disclosed technique.

Another method for stabilizing a tissue support structure exhibiting the parallel lines configuration is periodically coupling supporting thread sections across a group of a selected number of threads (i.e., it could be across all of the threads of the tissue support structure). In such cases, the number of intersections is greater than zero but still sub-stantially small (i.e., the intersection density is below 10,000). Reference is now made to FIG. 2G, which is a schematic illustration of a tissue support structure, generally referenced 310, constructed and operative in accordance with another embodiment of the disclosed technique. Tissue support struc-ture 310 includes a plurality of parallel non-braided monofilament threads, such as thread 314. At least two threads in each group of a selected number of threads, such as exemplary group 312 (e.g., which includes five threads) is coupled with a supporting thread section, such as supporting thread sections 316. For example, group 312 is affixed to supporting thread sections (e.g., by molding or sintering). Supporting thread section 316 is also made of a non-braided monofilament thread. These support thread sec-tions provide structural support to the parallel threads with-out substantially increasing the number of thread intersec-tions.

The matrix configuration, as mentioned above, is described herein with reference to FIGS. 3A-3D, to which reference is now made. FIGS. 3A-3D are schematic illustra-tions of an implantable, incorporable and non-reactive tissue support structure exhibiting the matrix configuration, gener-ally referenced 320, constructed and operative in accordance with a further embodiment of the disclosed technique. Tissue support structure 320 includes a network of singular non-braided monofilament threads, such as non-braided monofilament thread 322. The singular non-braided mono-filament threads are configured such that sections of a portion of the threads are parallel to and equidistant from sections of other threads (e.g., sections 324i, 3242, 3243 and 3244). Furthermore, sections of the remaining portions of the thread cross sections of other threads (e.g., section 3245 crosses sections 3241, 3242, 3243 and 3244) at intersections such as intersection 326. An intersection is defined as the crossing of two thread sections, which are non-affixed, loosely affixed or firmly affixed at their crossing. Thus, the intersecting thread sections define a plurality of spaces, such as space 328, which exhibit substantially the shape of a square. Thread 322 is a wide bore thread. For example, thread 322 may be a #0 (e.g., 0.35 millimeters in diameter) non-braided monofilament nylon thread (e.g., polyamide 6 or similar material).

a blown up perspective view of a single space 328. Thread 322 is attached to sections of other threads at intersections such as intersection 326. the thread sections are firmly affixed by molding the thread sections. However, it is noted that the thread sections may be fused or otherwise affixed in an end-to-side, right-angled, grid-like fashion at regularly spaced intersections. The thread 322 may be fused at intersection 326 by an initial molding process or by heat or other known methods for fusing threads, such as nylon threads.

Figure 3A:
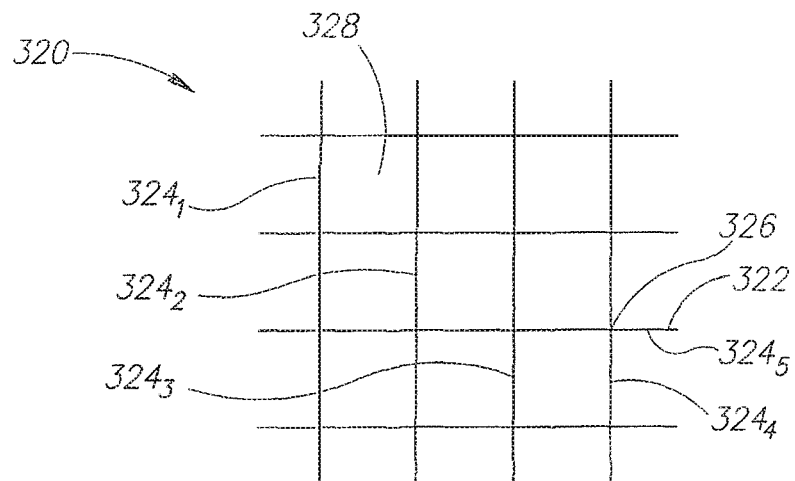
FIGS. 3A-3D are schematic illustrations of an implantable, incorporable and non-reactive tissue support structure exhibiting the matrix configuration, constructed and operative in accordance with a further embodiment of the disclosed technique.
Figure 3B:
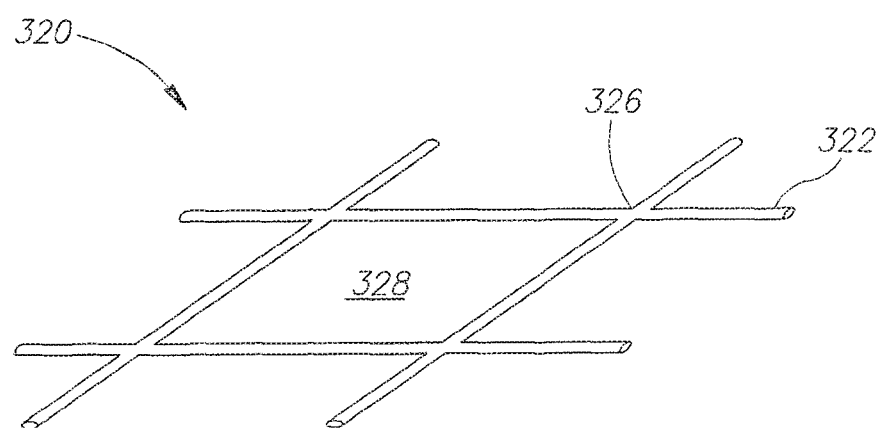
Figure 3C:
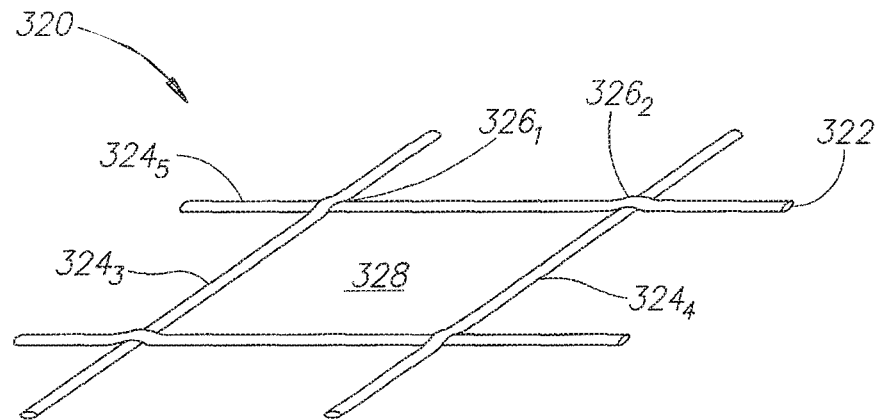
Figure 3D:
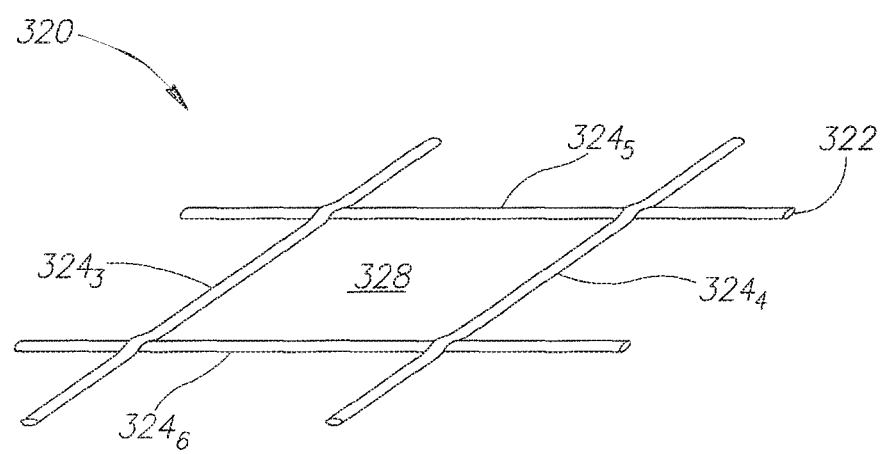

FIG. 3C depicts another blown up perspective view of space 328. In FIG. 3C, the sections of thread 322 are woven into a regularly spaced matrix form in which "horizontal" section 3245 (i.e., the weft) overlays a "vertical" section 3244 (i.e., the warp) at one intersection 3262 but lies under the next "vertical" section 3243 at the next intersection 3261. FIG. 3D depicts space 328 where "vertical" sections 3243 and 3244 are laid upon the "horizontal" sections 3245 and 3246 or vice versa without weaving. The "vertical" sections are simply placed on top of the "horizontal" sections.

The inner dimensions of the repetitive square matrix spaces, such as space 328, described hereinabove in conjunction with FIGS. 3A-3D (i.e., excluding the dimensions of thread 322) are, for example, 0.5×0.5 cm, 0.8×0.8 cm, 2.0×2.0 cm or 3.0×3.0 cm. Other sizes are possible. The spaces need not necessarily be perfect, rigid squares. The aforementioned dimensions of the squares result in an intersection density of only 400, 160, 25 and 10, respectively.

Figure 4A:
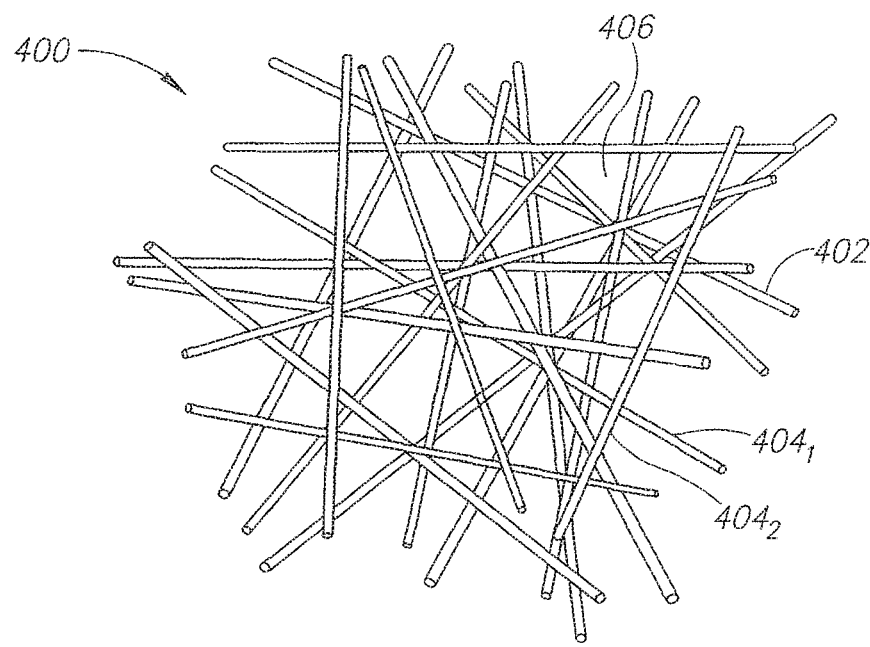
FIGS. 4A-4B are schematic illustrations of an implantable, incorporable and non-reactive tissue support structure exhibiting the randomly intersecting lines configu-ration, constructed and operative in accordance with another embodiment of the disclosed technique.
Figure 4B:
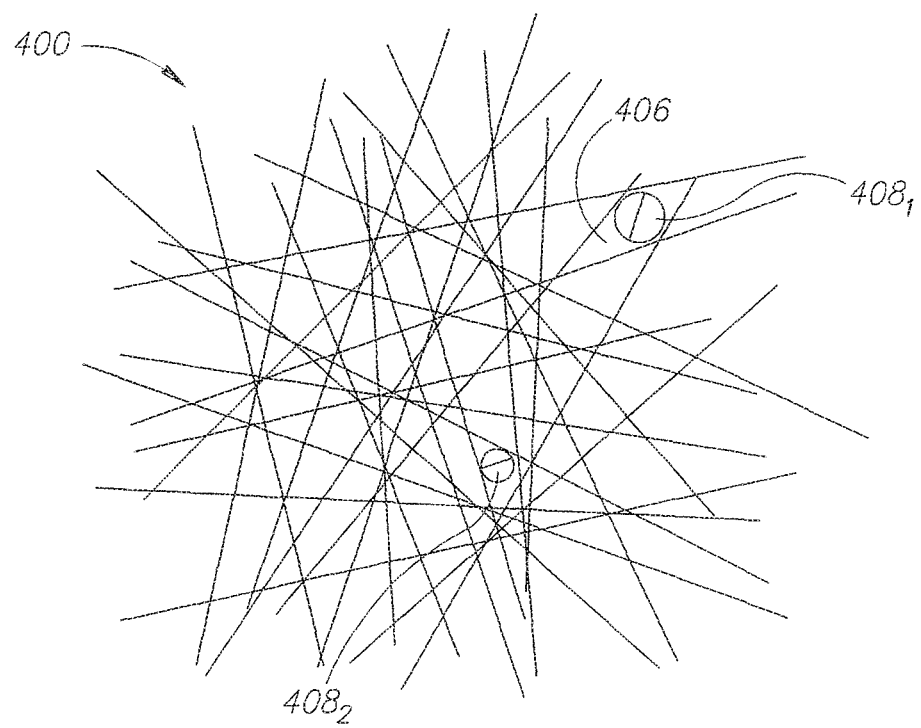

The randomly intersecting threads configuration, as mentioned above, is schematically illustrated in FIG. 4A. Reference is now made to FIG. 4A, which are schematic illustrations of an implantable, incorporable and non-reactive tissue support structure exhibiting the randomly intersecting lines configuration, generally referenced 400, constructed and operative in accordance with another embodiment of the disclosed technique. Tissue support structure 400 includes a singular, non-braided monofilament thread 402, arranged such that sections of the thread (e.g., sections 4041 and 4042) randomly overlay or underlay other sections of the thread. The end result appears as if the sections of thread were randomly woven. The thread sections may be firmly coupled with each other at the intersection point thereof as described above. the randomly intersecting sections of the thread produce a plurality of spaces, such as space 406. Tissue support structure 400 may be defined by the maximal and average dimensions of the spaces. For example, in a structure with small spaces, the largest space shall admit there through an imaginary circle 4081 of no more than approximately 1.0 cm diameter, and the estimated average space shall admit there through an imaginary circle 4082 of approximately 0.5 cm diameter. In a structure with larger spaces, the imaginary circles may be 4.0 cm and 2.0 cm in diameter for the largest and average spaces, respectively. Other dimensions and other shapes are possible.

It is noted that the tissue support structure according to the disclosed technique includes between 0 and 10,000 thread intersections per 100 cm2 irrespective of the size or shape of the structure. Furthermore, It is also noted that any of the configurations of the disclosed technique (e.g., randomly intersecting lines) may also include a stabilizing perimeter structure as described above with reference to FIGS. 2A-2F and further elaborated below.

A tissue support structure, exhibiting the form of a hub and radiating spokes and concentric rings, is schematically illustrated in FIGS. Reference is now made to FIGS. which are schematic illustrations of an implantable, incorporable and non-reactive tissue support structure exhibiting the hub and radiating spokes configuration, generally reference 500, constructed and operative in accordance with a further embodiment of the disclosed technique. FIG. depicts a top view of tissue support structure 500 and is a perspective view of tissue support structure 500. FIGS. depict tissue support structure 500 (e.g., for hernia repair), which includes a plurality of singular non-braided monofilament threads such as thread 502, made of, for example, #0 monofilament nylon threads, and a central hub 504. The threads are coupled with hub 504 at one end thereof to form spokes radiating out from central hub 504. Hub 504 is made of nonreactive, sterilizable, degradation-resistant, elastic, non-carcinogenic materials (e.g., nylon, metals, carbon amalgams, silicon and other suitable materials). In FIGS, hub 504 exhibits a circular shape. However, hub 504 may exhibit any other suitable shape. The spokes may be equally spaced around the hub or grouped into sectors.

Reference is now made to FIGS, which are schematic illustrations of an implantable, incorporable and non-reactive tissue support structure, exhibiting a hub and radiating spokes configuration with concentric rings, generally referenced 520, constructed and operative in accordance with another embodiment of the disclosed technique. FIG. is a top view of tissue support structure 520 and is a perspective view of tissue support structure 520. Tissue support structure 520 includes a plurality of threads such as a thread 522, a central hub 523 and at least one concentric ring of thread such as a concentric ring 526. The threads are coupled with central hub 523 at one end thereof and extend radially therefrom, thus forming spokes. The concentric rings are coupled with the spokes at various intervals 524i, 5242, 5243, 5244, 5245 and 5246 around hub 523 and are typically of the same material as the threads. However, other inert materials may be employed. The threads are, for example, lines of #0 monofilament nylon threads. The concentric rings, such as concentric rings 526, serve as stabilizing support for the tissue support structure 520. A perimeter concentric ring 528, coupled with the spokes at the other end thereof, may be of thicker cross-section to increase the stability of tissue support structure 520.

According to one alternative, concentric rings 526 are coupled with the threads (e.g., thread 522) by alternately placing concentric rings 526 over and under the threads. According to another alternative, concentric rings 526 are placed on one side of the threads. All concentric rings may be placed on the same side of the threads, or alternating rings may be placed on alternating sides. Concentric rings 526 may be affixed to the threads, for example, by fusing, soldering or sintering concentric rings 526 to the threads as further explained with reference to FIG. 10. A various number of concentric rings may be place at various intervals (e.g., 5241 and 5242) there between. In general, the dimensions of the resulting spaces, such as space 532, are within pre-determined upper limits. For example no space shall exhibit dimensions greater than 0.5×1.0 cm or 1.0×2.0 cm so as to prevent substantial tissue herniation. The outermost concentric ring, which is also the perimeter of tissue support structure 520, exhibits a diameter such as 18 cm, 20 cm, 30 cm or any other suitable diameter.

The hub and radiating spokes with concentric rings embodiment may be floppy (i.e., with low tautness) like a spider-web, having increased compliance with abdominal wall forces. Alternatively, a tissue support structure according to the hub and radiating spokes with concentric rings embodiment may be substantially taut and rigid. Tautness may not be uniform throughout the structure. Floppiness and tautness are determined by the lengths of the spokes in relation to the radius of the stabilizing perimeter structure (as described below in FIGS. 7A-7C regarding invertible convexity) and by the tautness of the inter-spoke intervals of the concentric rings (e.g., 5301, 5302, 5303, 5304 and 5305). In all cases, the intersection density of the hub and radiating spokes with concentric rings tissue support structure is small relative to known in the art meshes.

A plurality of tissue support structures exhibiting the hub and radiating spokes configuration, such as described in conjunction with FIGS, may be combined to form a tissue support structure array. Reference is now made to FIG. which is a schematic illustration of an implantable, incorporable and non-reactive tissue support structure array made of a plurality of hub with radiating spokes tissue support elements, generally referenced 540, constructed and operative in accordance with a further embodiment of the disclosed technique. Tissue support structure array 540 is formed from a plurality of tissue support elements thus creating a tissue support structure array 540. Tissue support structure array 540 is produced by intersecting the spokes of different tissue support structures such as tissue support structures 542, 544 and 546. Each one of tissue support elements 542, 544 and 546 is similar to tissue support structure 500. Such a tissue support structure array may have a perimeter (which is circular, elliptical or quadrilateral in shape) whose diameter may typically be either 20 cm or 30 cm across. Concentric rings (not shown) or other shaped structures may be added as necessary to limit the sizes of intervening spaces.

Figure 5A:
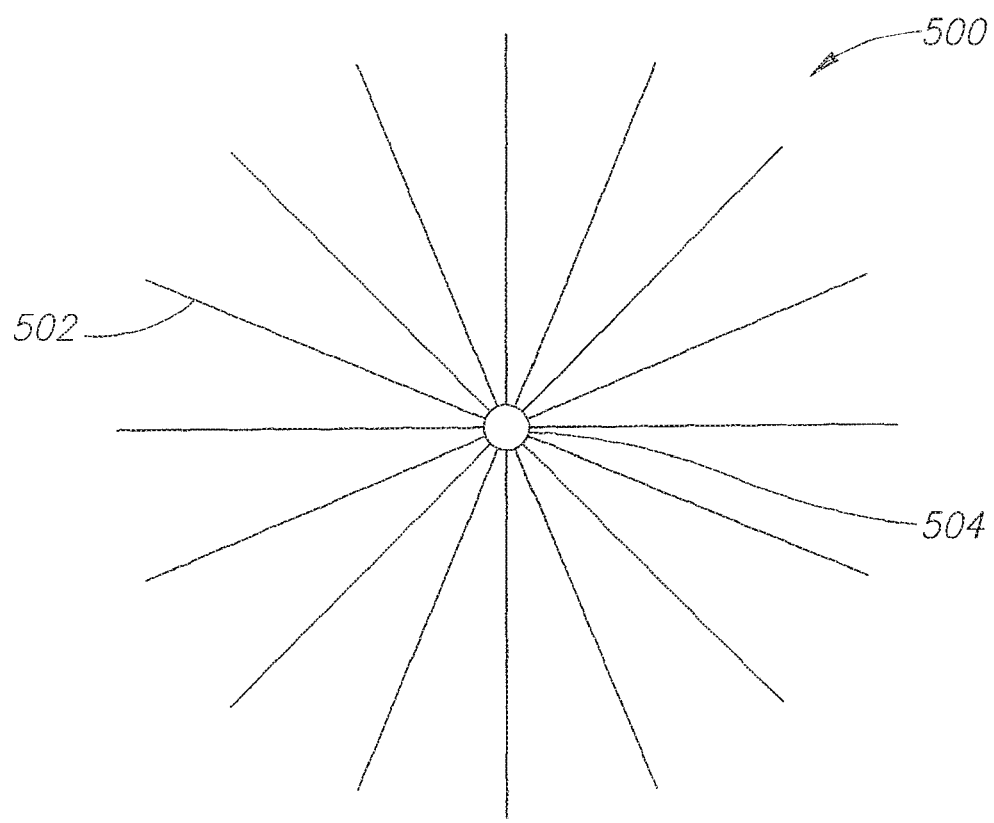
FIGS. 5A-5B are schematic illustrations of an implantable, incorporable and non-reactive tissue support structure exhibiting the hub and radiating spokes configura-tion, constructed and operative in accordance with a further embodiment of the disclosed technique.
Figure 5B:
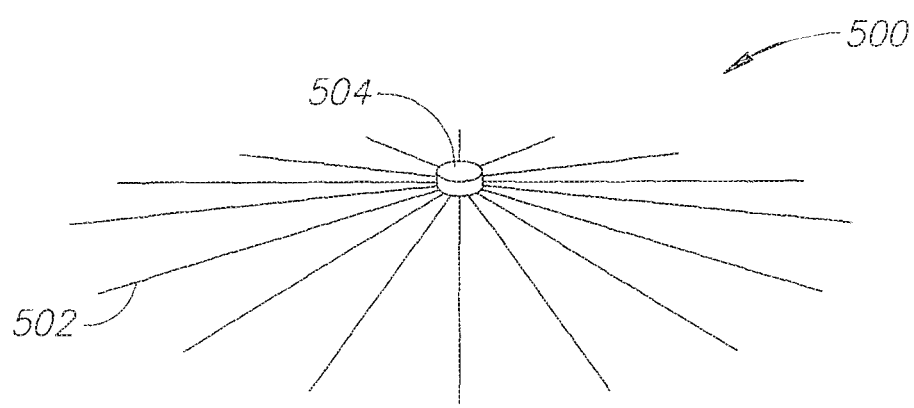
Figure 5C:
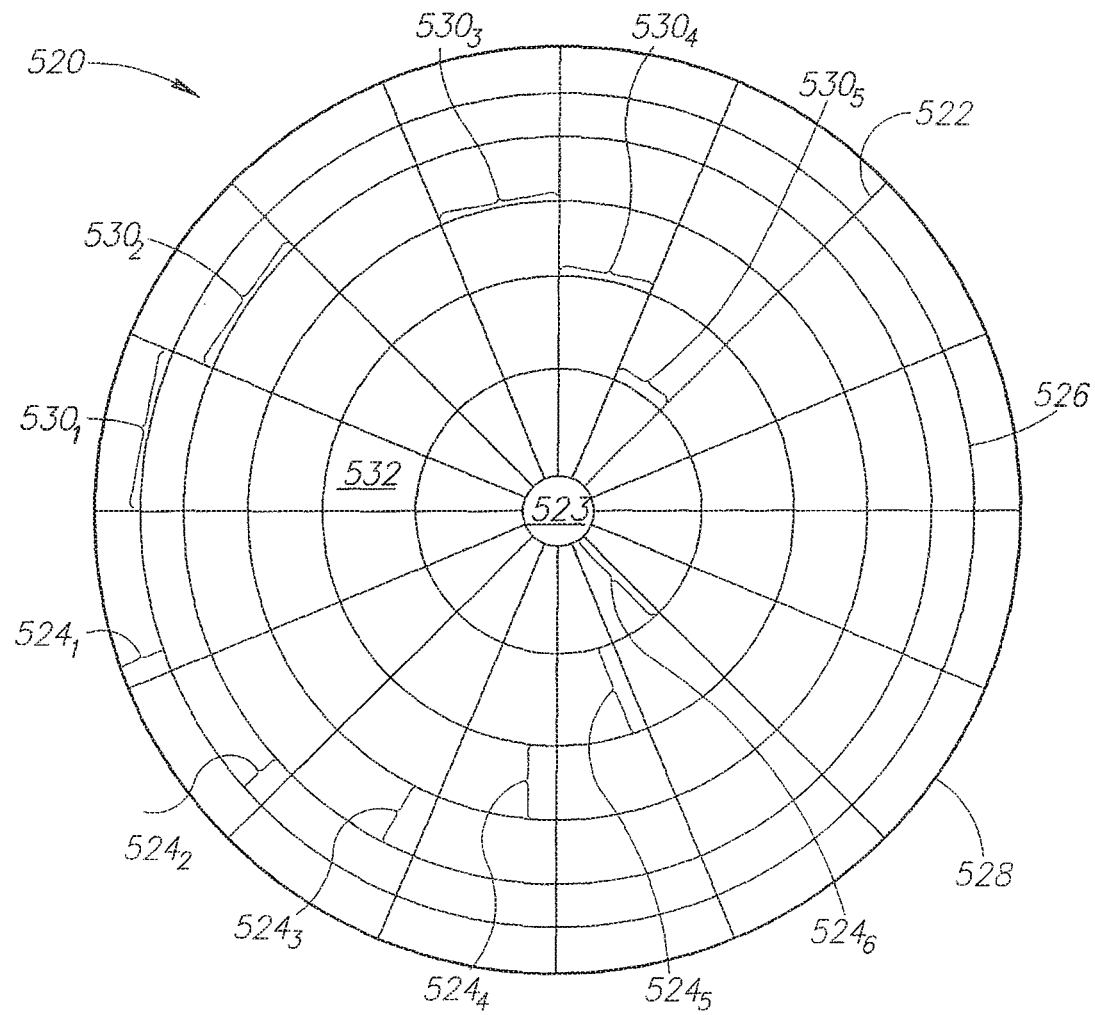
FIGS. 5C-5D, which are schematic illustrations of an implantable, incorporable and non-reactive tissue support structure exhibiting a hub and radiating spokes configuration with concentric rings, constructed and operative in accor-dance with another embodiment of the disclosed technique.
Figure 5D:
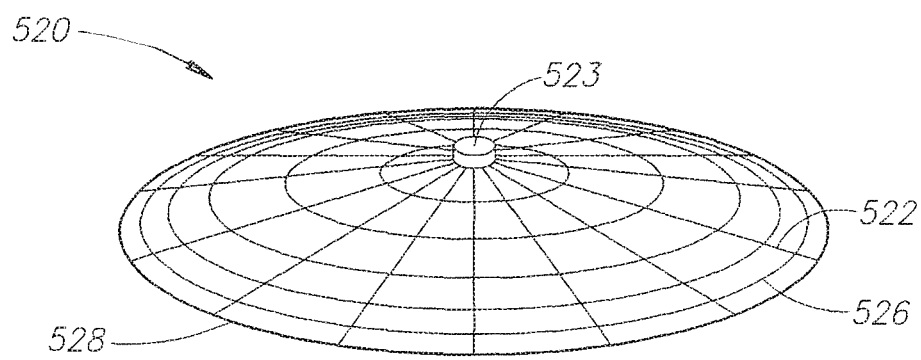
Figure 5E:
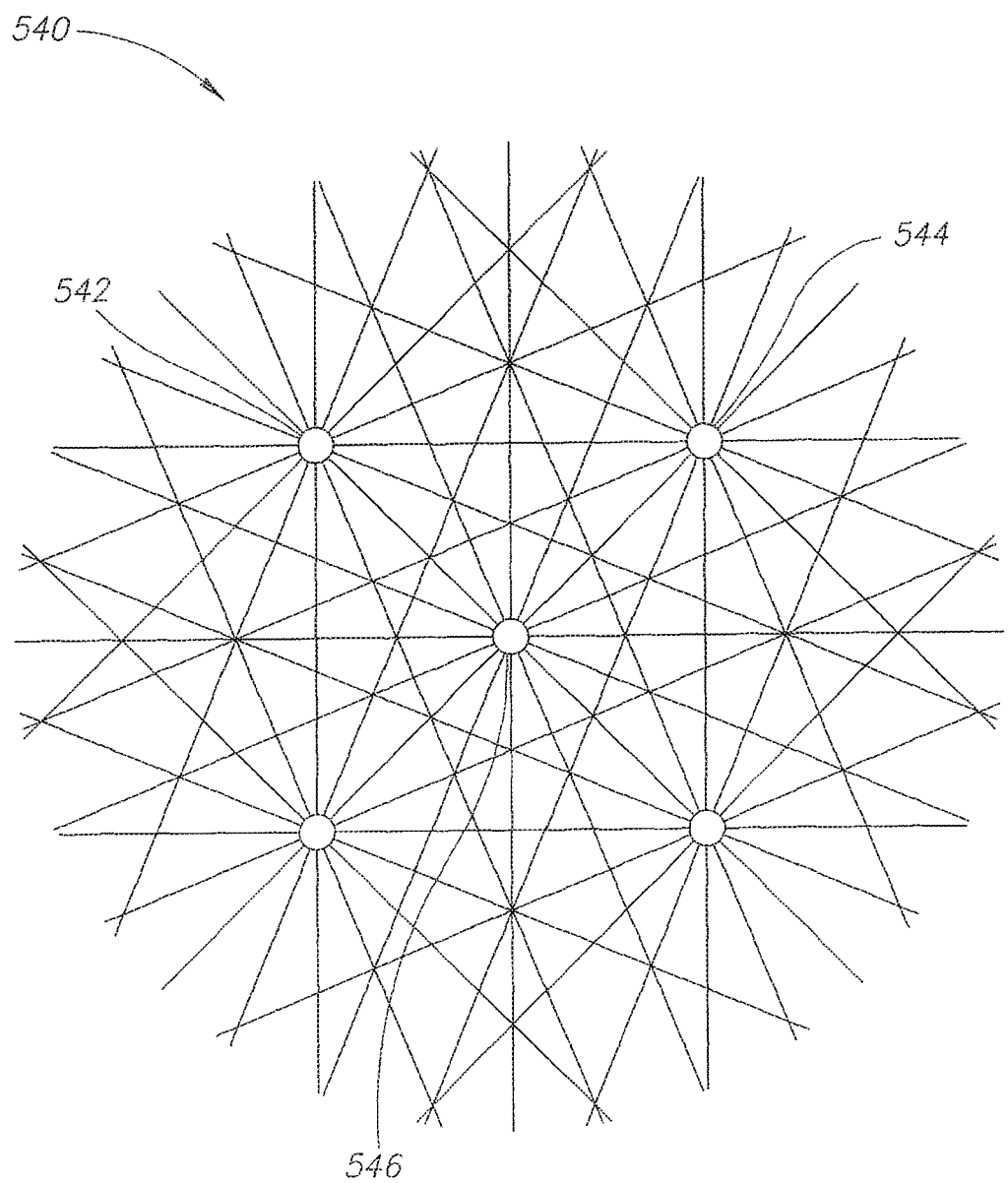
FIG. 5E, which is a schematic illustration of an implantable, incorporable and non-reactive tissue support structure array made of a plurality of hub with radiating spokes tissue support structures, constructed and operative in accordance with a further embodiment of the disclosed tech-nique.
Figure 6A:
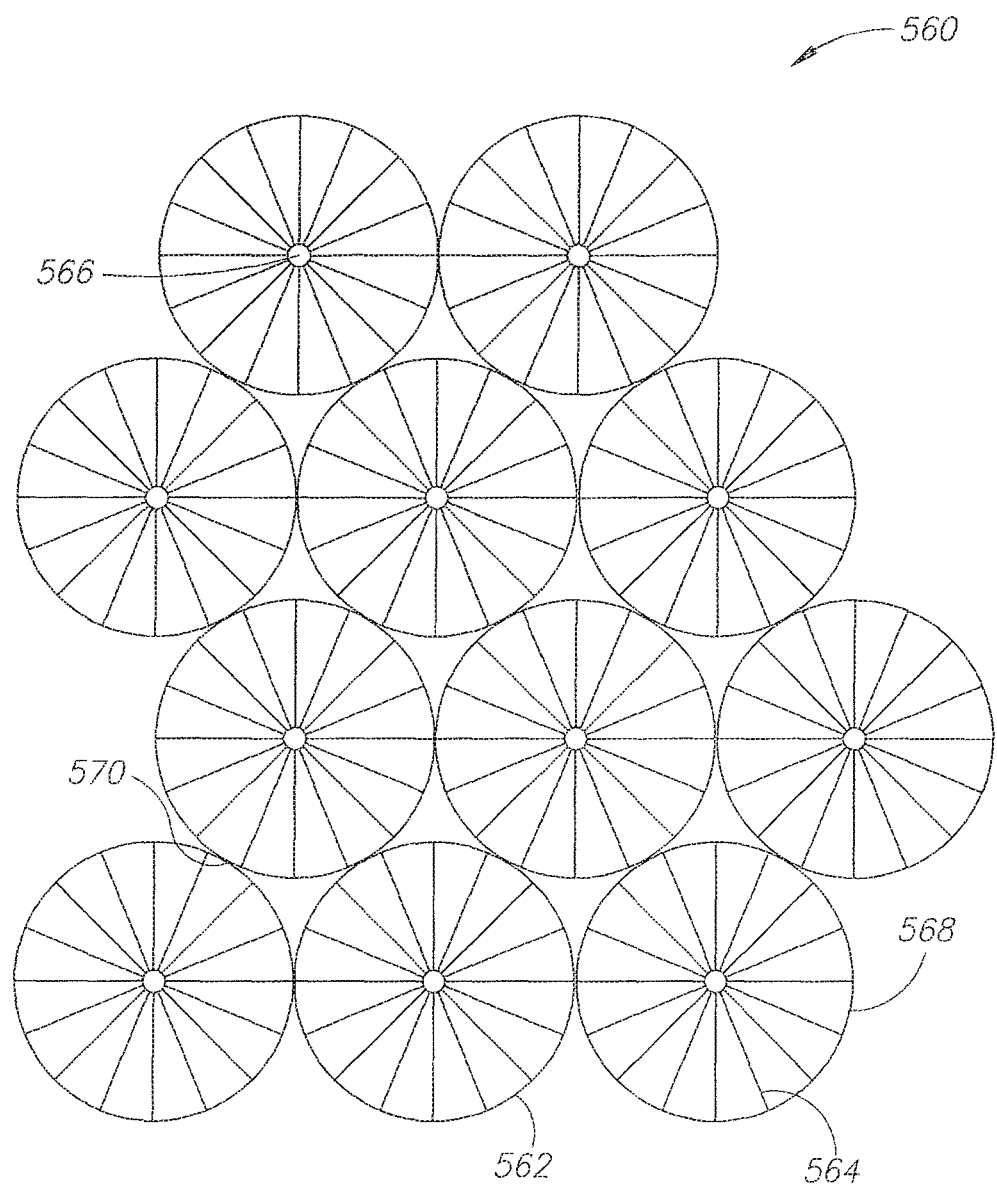
FIGS. 6A-6B is schematic illustration of an implantable, incorporable and non-reactive tissue support structure array made of quilted hubs with radiating spokes tissue support structures, constructed and operative in accor-dance with another embodiment of the disclosed technique.
Figure 6B:
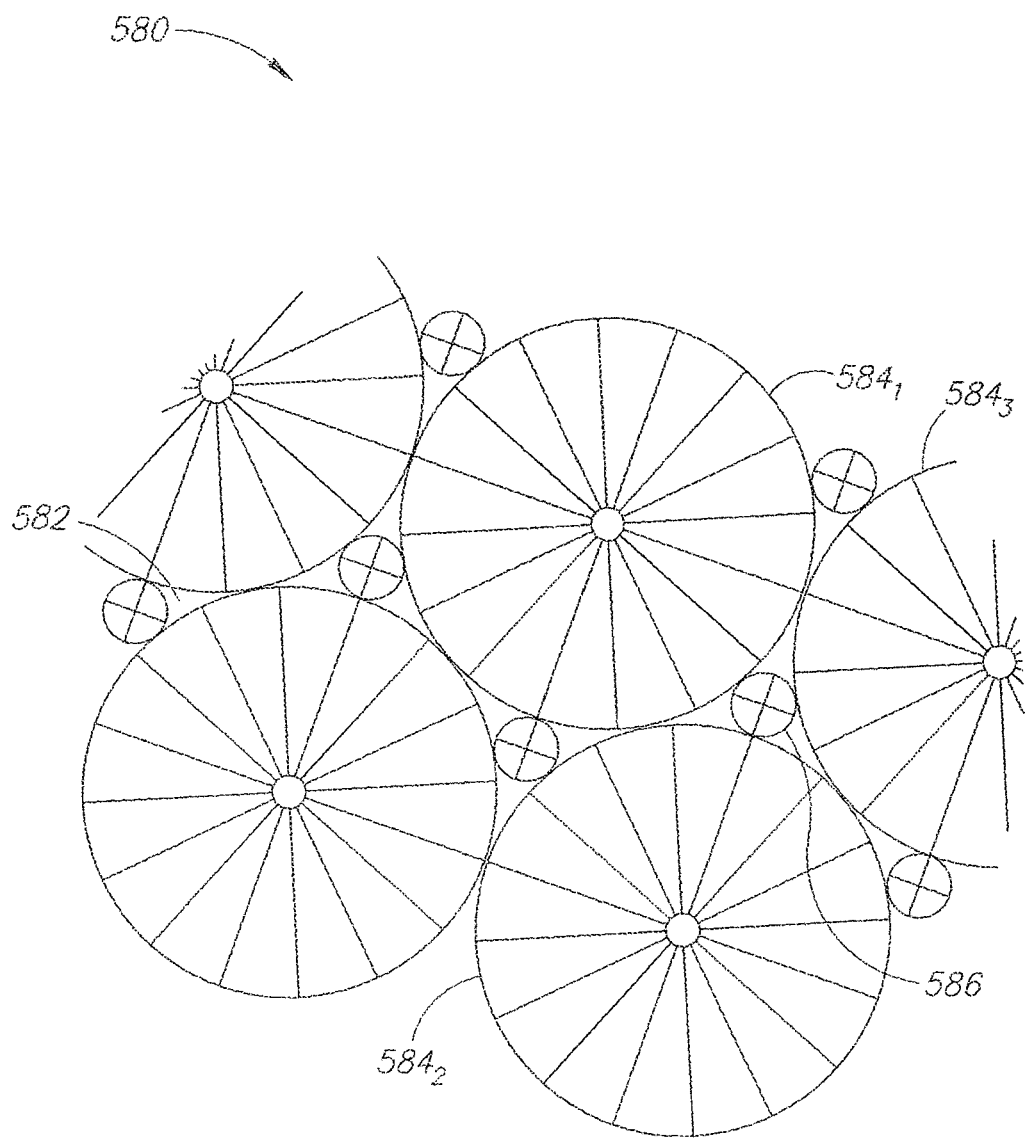

The following description in conjunction with FIGS. 6A-6B relates to the quilted hubs with radiating spokes configuration. Reference is now made to FIGS. 6A-6B, which is schematic illustration of an implantable, incorporable and non-reactive tissue support structure array made of quilted hubs with spokes tissue support structures, generally referenced 560 and 580 respectively, constructed and operative in accordance with another embodiment of the disclosed technique. With reference to FIG. 6A, tissue support structure array 560 is made of a plurality of tissue support structures, such as tissue support structure 562. Tissue support structure 562 is similar to tissue support structure 500 (FIG. 5A). Each tissue support structure includes a plurality of threads such as thread 564, a central hub such as central hub 566 and a stabilizing perimeter structure such as stabilizing perimeter structure 568. The threads are coupled at one end thereof to a respective central hub and at the other end to a respective stabilizing perimeter structure. The respective stabilizing perimeter structures are all coupled at contact points, such as contact point 570, in a "quilted" fashion between the respective stabilizing perimeter structures thereof. It is noted that tissue support structure 560 does not generally need concentric rings due to the smaller diameter of each stabilizing perimeter structure 568. The diameter of all of the stabilizing perimeter structures is typically either 5 cm or 8 cm in diameter, and can be identical or vary throughout the quilt. It is further noted that the diameter of a tissue support structure in quilted hubs with radiating spokes tissue support structure array 560 is generally smaller than the diameter of the single hub and radiating spokes with concentric rings described hereinabove in conjunction with FIGS. 5A-5D.

With reference to FIG., tissue support structure array 580 is similar to tissue support structure array 560 (FIG. 6A). However, the spaces 582 between the coupled stabilizing perimeter structures, such as stabilizing perimeter structures 5841, 5842, 5843 may be filled by smaller tissue support structure such as tissue support structure 586, to limit the size of any open spaces 582 (e.g., to less than 1.0 cm in diameter). The diameter of tissue support structure 586 is smaller than the diameter of tissue support structure 5841 and thus requires fewer spokes to prevent tissue herniation. Alternatively, tissue support structure 586 may include only a ring with spokes (i.e., without a hub). Nevertheless, tissue support arrays 560 and 580 are constructed while maintaining an intersection density to be no larger than 10,000 intersections per 100 cm2.

Figure 7A:
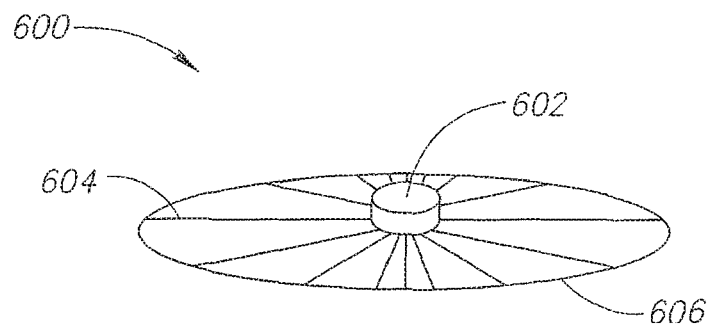
FIGS. 7A-7D are schematic illustrations of implant-able, incorporable and non-reactive tissue support structures exhibiting invertible convexity, constructed and operative in accordance with a further embodiment of the disclosed tech-nique.
Figure 7B:
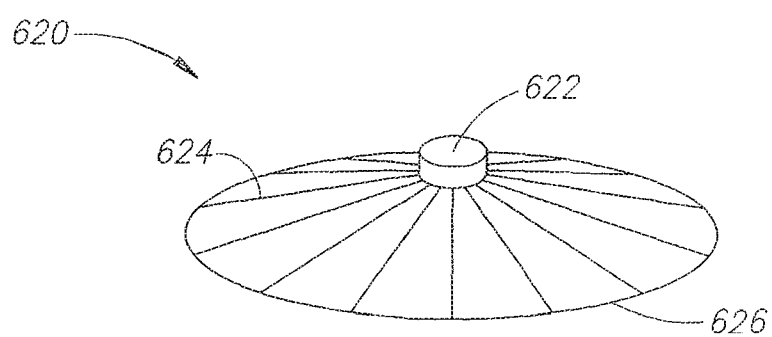
Figure 7C:
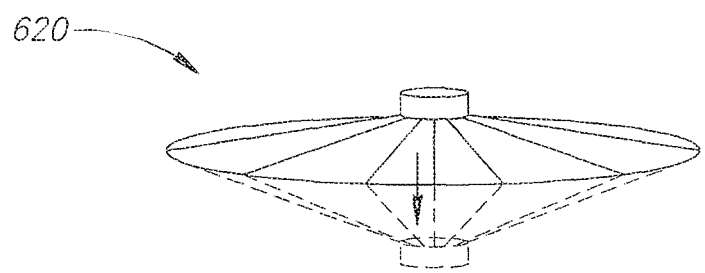

Reference is now made to FIGS. 7A-7D, which are schematic illustrations of implantable, incorporable and non-reactive tissue support structures exhibiting invertible convexity, generally referenced 600 and 620 respectively, constructed and operative in accordance with a further embodiment of the disclosed technique. FIG. 7A refers to tissue support structure 600 and FIG. 7C refer to tissue support structure 620. With reference to FIG. 7A, the diameter defined by a hub 602 plus twice the length of a thread 604 is equal to the diameter of stabilizing perimeter structure 606. Thus, hub 602, the threads and circular stabilizing perimeter structure 606 are all located on the same plane. With reference to FIGS. 7B and 7C, the diameter defined by hub 622 plus twice the length of a thread 624 is larger than the diameter of stabilizing perimeter structure 626. Thus, hub 622 and stabilizing perimeter structure 626 can be located in different planes. This results in hub 622 and the threads such as thread 624 being slightly convex in relation to the plane of stabilizing perimeter structure 626. Hub 622, and thus the convexity, alternates between the two sides of the plane defined by stabilizing perimeter structure 626 in response to the physiologic forces of the abdominal wall, and is referred to herein as "invertible convexity" (FIG. 7C).

Figure 7D:
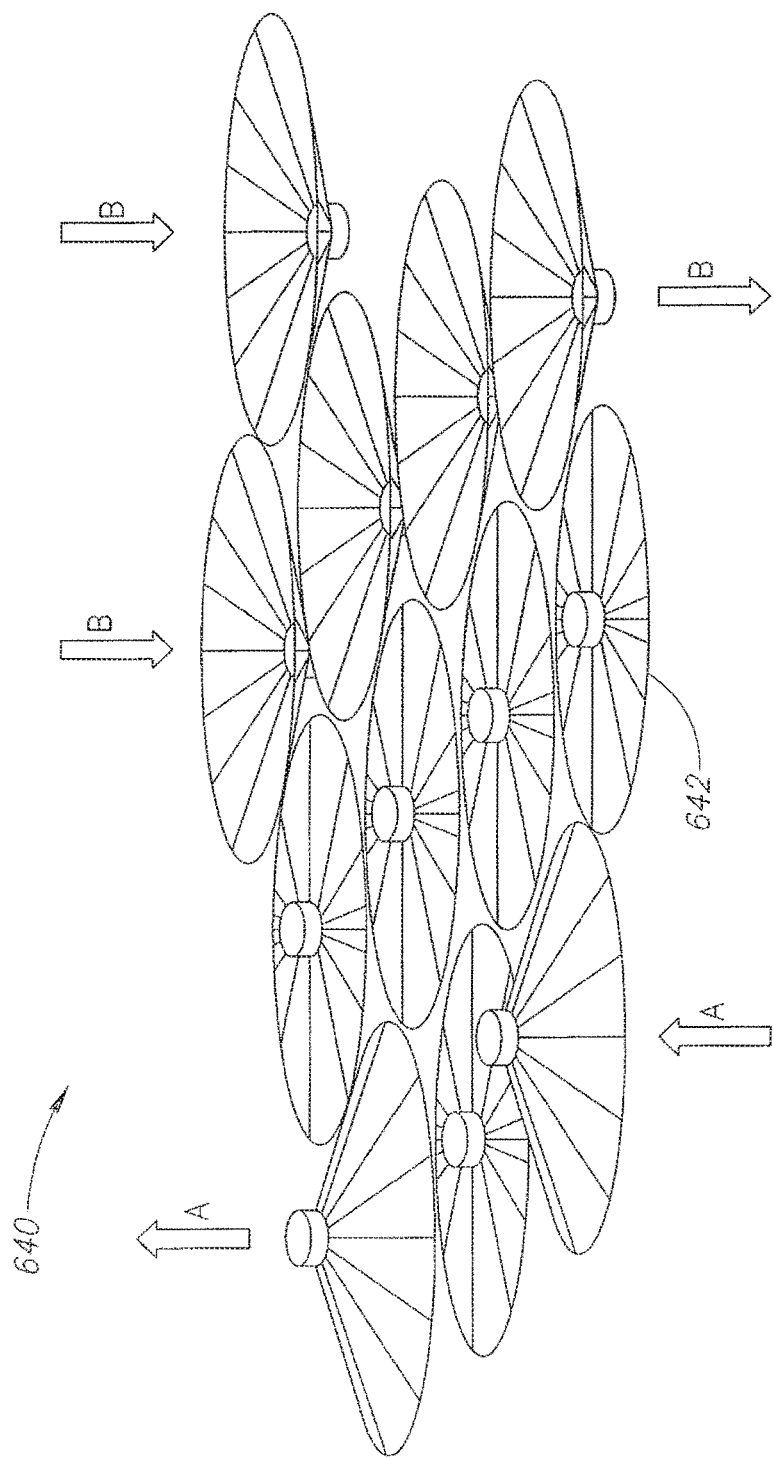

Each tissue support structure of the tissue support structure array 560 described hereinabove in conjunction with FIG. 6A, may exhibit an invertible convexity as described above. With reference to FIG. 7D, tissue support structure array 640 is constructed from a plurality of tissue support structures, such as tissue support structure 642 which is similar to tissue support structure 620 (FIGS. 7B and 7C). Due to the invertible convexity of each tissue support structure in tissue support structure array 640, the surface of tissue structure array 640, the surface of tissue support structure array 640 readily responds to varying physiologic forces simultaneously acting there upon. For example, these forces may press out in one region (e.g., as demonstrated by arrows A), and pull in (e.g., as demonstrated by arrows B), in another region. Such forces are applied normally over the abdomen wall, and normally cause the abdominal wall to undulate subtly. Tissue support structure array 640 with invertible convexities is thus designed to allow the post-repair abdominal wall to respond to biologic stresses by undulating normally and thus avoiding the "stiff abdomen" syndrome. The size of each stabilizing perimeter structure 642 may exhibit several sizes, for example, 5 cm or 8 cm. The overall size of the tissue support structure array 640 may be, for example, 20×20 cm or 30×30 cm, though it can be made smaller or larger. The individual circles are typically identical in size, but need not be necessarily.

As mentioned above, the tissue support structure according to the disclosed technique may be structurally stabilized. Various stabilizing techniques may be employed. The threads of tissue support structures according to the disclosed technique may be affixed without the addition of a separate stabilizing structure or structures (e.g., perimeter structures), for example, by affixing threads to each other at their inter-sections (e.g., as described with reference to FIG.). Sin-gular monofilament nylon threads can be fused or molded to other threads at right-angles in an end-to-side manner to produce an essentially flat grid. Existing manu-factur-ing processes for producing such grid-like structures may be applied to #0 monofilament nylon thread. Threads may be affixed at intersections thereof in additional ways, for example, by sintering. Also, when different threads made of different materials are used, the temperature during the sintering process may be gradually increased to differen-tially including the melting points of some materials used, and thus to selectively affix the threads. Another example may employ reversible brief nylon dissolution processes, such as by heat or chemicals, which leave the singular monofilament thread unchanged except for a 'soldering' effect at the precise points of contact. According to another example, selected points of contacts are individually sol-dered by a handheld or auto-mated electrode (i.e., when such affixing is sufficient) or by employing plastic adhesives resistant to both sterilization and the physiologic environ-ment. Other affixing options, such as fusion by molding, are possible.

Figure 8A:
FIGS. 8A-8D are schematic illustrations of different exemplary cross-sections of a stabilizing perimeter structure constructed and operative in accordance with another embodiment of the disclosed technique.
Figure 8B:
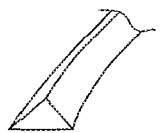
Figure 8C:
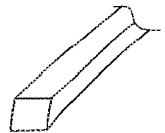
Figure 8D:

Furthermore, stabilization of singular monofila-ment threads to hubs and concentric rings (for example, FIG. 8C) may also be done by dissolution processes similar to those described above or by physically embedding the nylon threads into the nylon hubs using existing manufacturing processes, or by initial molding. Concentric rings may be stabilized with the threads by affixing contact points as described above with reference to stabilizing a thread to another thread.

When a perimeter structure is added to the tissue support structure, the perimeter structure generally defines the shape of the tissue support structure in addition to provid-ing stabilization. Reference is now made to FIGS. 8A-8D, which are schematic illustrations of different exemplary cross-sections of a stabilizing perimeter structure con-structed and operative in accordance with another embodi-ment of the disclosed technique. This perimeter structure may be for example structure 204, in FIG. 2A, structure 262 in FIG. 2D, or structure 528 in FIG. 5C. FIG. 5A depicts a circular cross-section, FIG. depicts a triangular cross-sec-tion, FIG. 5C depicts a square cross-section and FIG. 5D depicts a rectangular cross-section. The stabilizing perimeter structures may be hollow or solid. Also, depending on the function and form of the tissue support structure, the stabi-lizing perimeter struc-ture may be a #0 thread of 0.35 mm cross-section (e.g., rollable for laparoscopy), or, for example, exhibit a 1.0 cm×1.0 cm cross section. The stabi-lizing perimeter structure may exhibit different dimensions, for example, between 15 cm and 40 cm in diameter for circles or in side-length for quadrilaterals.

Figure 9A:
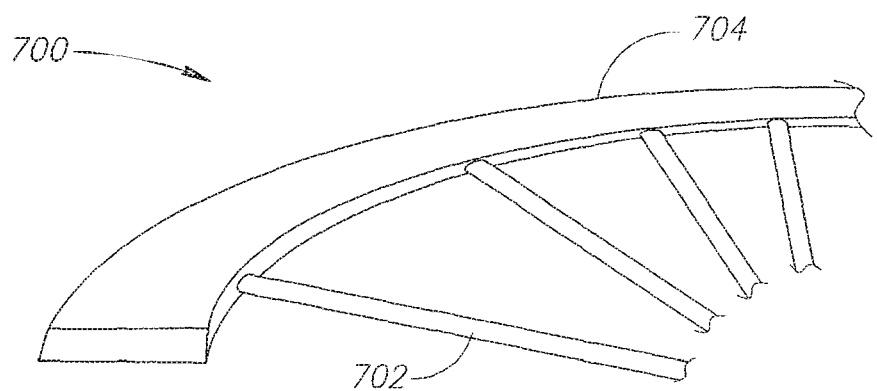
FIGS. 9A and 9B are schematic illustrations of a section of an implantable, incorporable and non-reactive tis-sue support structure constructed and operative in accordance with a further embodiment of the disclosed technique.
Figure 9B:
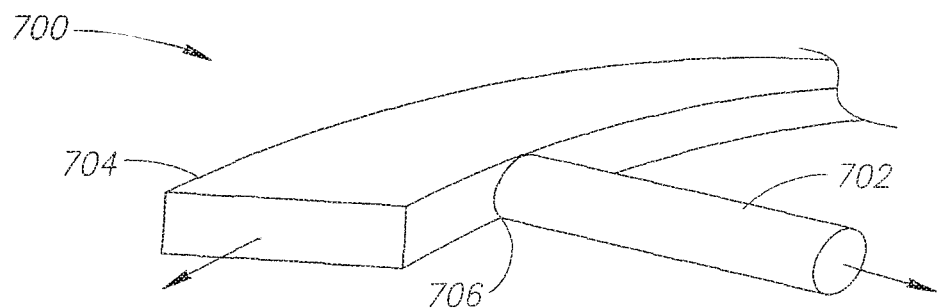

Stabilizing perimeter structures are typically made of synthetic and nonreactive, sterilizable, resistant to degra-dation, flexible, non-breakable under stress and non-carcino-genic materials such as nylon, metals, carbon amalgams and silicon. Stabilizing perimeter structures should also be suit-able for attaching singular monofilament threads (e.g., #0 nylon threads) thereto by, for example, soldering or initial molding. Reference is now made to FIGS. 9A and 9B which are schematic illustrations of a section, generally referenced 700, of an implantable, incorporable and non-reactive tissue support structure constructed and operative in accordance with a further embodiment of the disclosed technique. Sec-tion 700 includes a plurality of threads, such as a thread 702, coupled with a stabilizing perimeter structure 704. In FIG. 9A, the thickness of stabilizing perimeter structure 704, which exhibits a rectangular cross-section, is equal to the diameter of mono filament thread 702 coupled therewith. FIG. 9B depicts an enlarged view of section 700. Coupling threads, such as thread 702, to rectangle stabilizing perim-eter struc-ture 704 of similar thickness generally minimizes the pres-ence of 'nooks and crannies' at a coupling point 706. It is noted that the cross-section of the stabilizing perimeter struc-ture may be non-rectangular (e.g., oval), while maintaining the aforementioned principal of the cou-pling point (i.e., main-taining a similar thickness). As men-tioned, the stabilizing perimeter structure may be molded in one piece with threads attached.

In some applications, stabilizing perimeter struc-tures should be rigid enough to provide overall structural integrity to the tissue support structure and yet be flexible enough to respond to abdominal wall kinetics, and even to be rolled up (with neither loss of shape memory' nor breaking), for example, for use in laparoscopic surgery.

Figure 10:
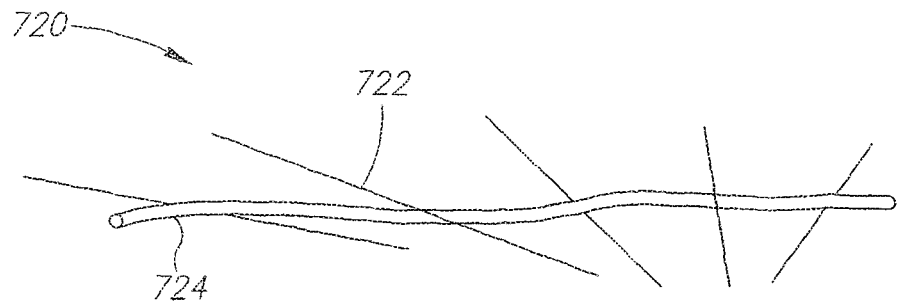
FIG. 10 is a schematic illustration of a section of an implantable, incorporable and non-reactive tissue support structure, constructed and operative in accordance with another embodiment of the disclosed technique.

Separate ring-like stabilizing structures, such as concen-tric ring 526 (FIGS. 8C-8D), may be layered onto, or woven into, the body of the tissue support structure. Refer-ence is now made to FIG. 10 which is a schematic illustration of a section, generally referenced 720, of an implantable, incor-porable and non-reactive tissue support structure, con-structed and operative in accordance with another embodi-ment of the disclosed technique. In FIG. 10, a ring stabilizing structure 724 is woven through threads such as a thread 722 of tissue support structure 720. Ring stabilizing structures 724 may exhibit various cross-sections (e.g., round, semicircular, or flat) to minimize nooks and crannies. Ring stabilizing structure 724 may be affixed to the tissue support structure by any of the above described methods (e.g., soldering or mold-ing).

A matrix tissue support structure such as described above in conjunction with FIG., is relatively independent of size or shape considerations when affixed firmly (e.g., molded) at each intersection of the threads. Thus, such a structure may be intra-operatively contoured to any shape and size, with-out reducing the stability thereof.

However, in the matrix embodiments described above in FIGS. 3C and 3D, the manufacturing step of weaving or layering the intersecting threads does not confer adequate stability. Affixing intersections to increase stability may be done as described above by the chemical or thermal "sol-dering" of intersections either universally by automotive pro-cesses (e.g., sintering), or individually by manual tech-niques. This results in a ready-made sheet of a network with "infinite" integral stability, which is also independent of size and shape considerations. The manufacturing process may be supplemented, for example, by affixing some or all of the intersections or by addition of separate perimeter stabilizing struc-tures or both.

The matrix tissue support structure may be attached to a stabilizing perimeter structure. The threads of the matrix may be embedded in, manufactured with or slung around the stabilizing perimeter structure. When a stabilizing perimeter structure is employed, the stability of the tissue support struc-ture is related to the size and shape of the stabilizing perimeter structure. Employing a stabilizing perimeter struc-ture pre-cludes intra-operative contouring, but provides a ready-to-use structure.

In the hubs with spokes and rings configuration, stabili-zation includes affixing the singular monofilament threads both into the central hub and into the perimeter ring struc-ture. In the former (i.e., coupling with the central hub), affixing may be done by embedding or molding, as part of the initial manufacturing process. In the latter (coupling with the perimeter ring structure), affixing may be done by techniques identical to those described with reference to FIGS. 9A and 9B. For stabilization of the concentric rings which are woven or laid onto the radiating spokes, affixing the contact point may be done between the two elements, as described above with reference to FIG. 10.

The quilted tissue support structure (FIG. 6A) may be obtained by coupling one perimeter structure to another by brief chemical or thermal dissolution, or by selec-tive manual soldering of contact points, or by the application of plastic adhesives. The space-filling miniature rings-with-spokes may similarly be affixed in place.

One of the advantages of the tissue support struc-tures according to the disclosed technique is the compliance to the physiological and the pathological strains and loads of the human body, such as those resulting from the active kinet-ics of the abdominal wall muscles or from passive responses of the abdominal wall to changes in intra-abdominal pressure. Increasing compliance in the tissue support structures accord-ing to the disclosed technique gives better dispersion of locally acting forces. This improves the adaptability of the tissue support structure to the host body and thus, for example, minimizes mesh disattachment with hernia recur-rences, as well as post-implantation pain syndromes relative to known in the art meshes.

The increased compliance of the tissue support structures according to the disclosed technique is due, inter alia, to the tension relation of the singular monofilament threads to the stabilizing perimeter structure. Thus, for example, when threads are stretched between a central hub and surrounding perimeter structure, compliance can depend on the tautness of the threads or on an invertible convexity design as described above.

When nylon threads are independently stretched across a perimeter structure, their compliance is inversely related to their tautness. Thus, the compliance of the structure may be adjusted by adjusting the tautness. When only a sepa-rate perimeter structure is used for matrix stabilization, pro-ducing a "closed" matrix, the singular monofilament threads may be stabilized solely by their affixing to the perimeter. This leaves the threads of the body of the matrix potentially very compliant, depending on the tautness of their 'stretch' across the overall surrounding perimeter structure. This simi-larly applies to the parallel lines configuration when stretch-ing parallel threads between the perimeter structures.

However, increasing thread compliance is more dif-ficult to achieve when a perimeter structure is not present, as in "open" matrices. In such configurations, which do not include a perimeter stabilizing structure, the stabilization of the tissue support structure depends on affixing the thread intersections. In these configurations, the compliance of the tissue support structure may be controlled by utilizing the principle that compliance is inversely related to the number and distribution (i.e., over the area of the matrix) of affixed intersections. Decreasing the number of affixed intersections distributed over the entire area of the matrix, results in increasing the number of non-affixed _intersections and thus in a more compliant structure.

Figure 11:
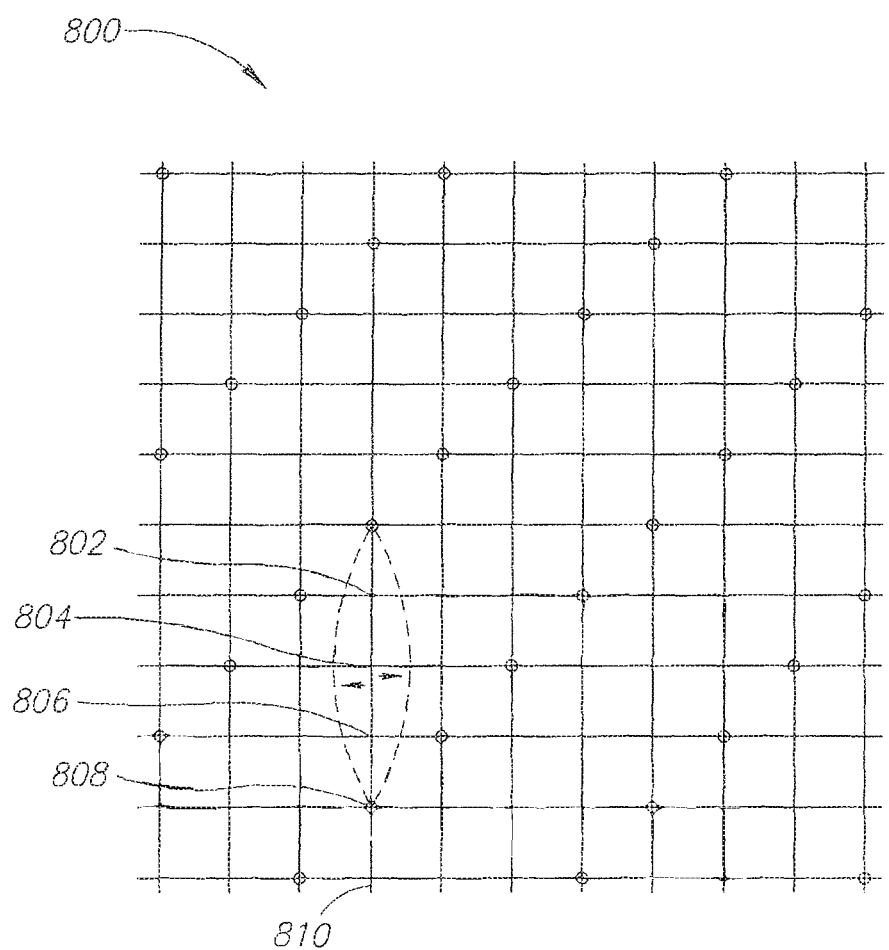
FIG. 11 is a schematic illustration of a tissue support structure, exhibiting the matrix configuration, constructed and operative in accordance with a further embodiments of the disclosed technique.

Reference is now made to FIG. 11, which is a sche-matic illustration of a tissue support structure exhibiting the matrix configuration, generally referenced 800, constructed and operative in accordance with a further embodiment of the disclosed technique. Tissue support structure 800 is similar to tissue support structure 320 (FIG. 3A). Tissue support struc-ture 800 includes three unfixed intersections, such as inter-sections 802, 804 and 806, for each one affixed inter-section such as intersection 808, along the length of any thread, such as a thread 810. In FIG. 11, affixed intersections are depicted by bold dots. The arrows and dotted lines show the direction and extent of the potential lateral motion of thread 810 (i.e., which represents the compliance thereof) in a representative segment affixed as described.

Figure 12A:
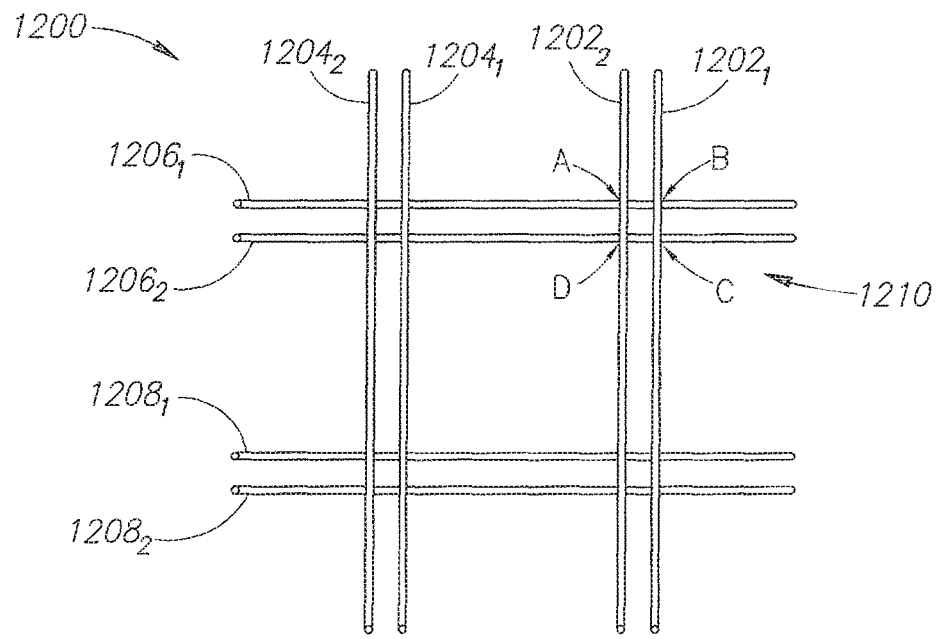
FIGS. 12A-12C are schematic illustrations of a tis-sue support structure constructed and operative in accordance with another embodiment of the disclosed technique.
Figure 12B:
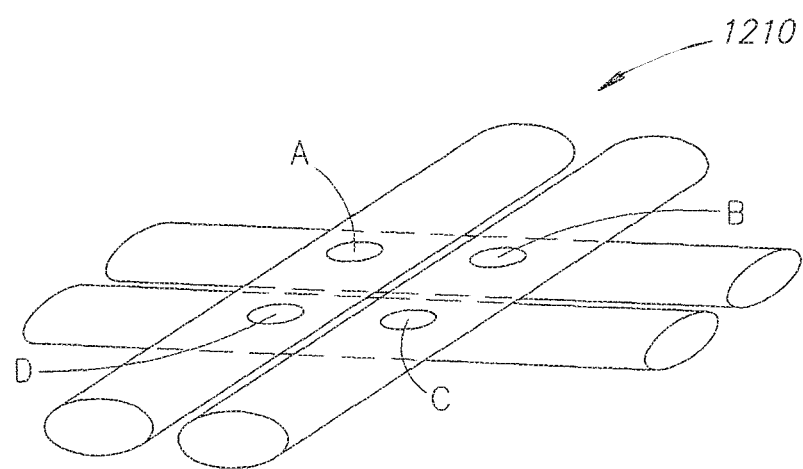
Figure 12C:
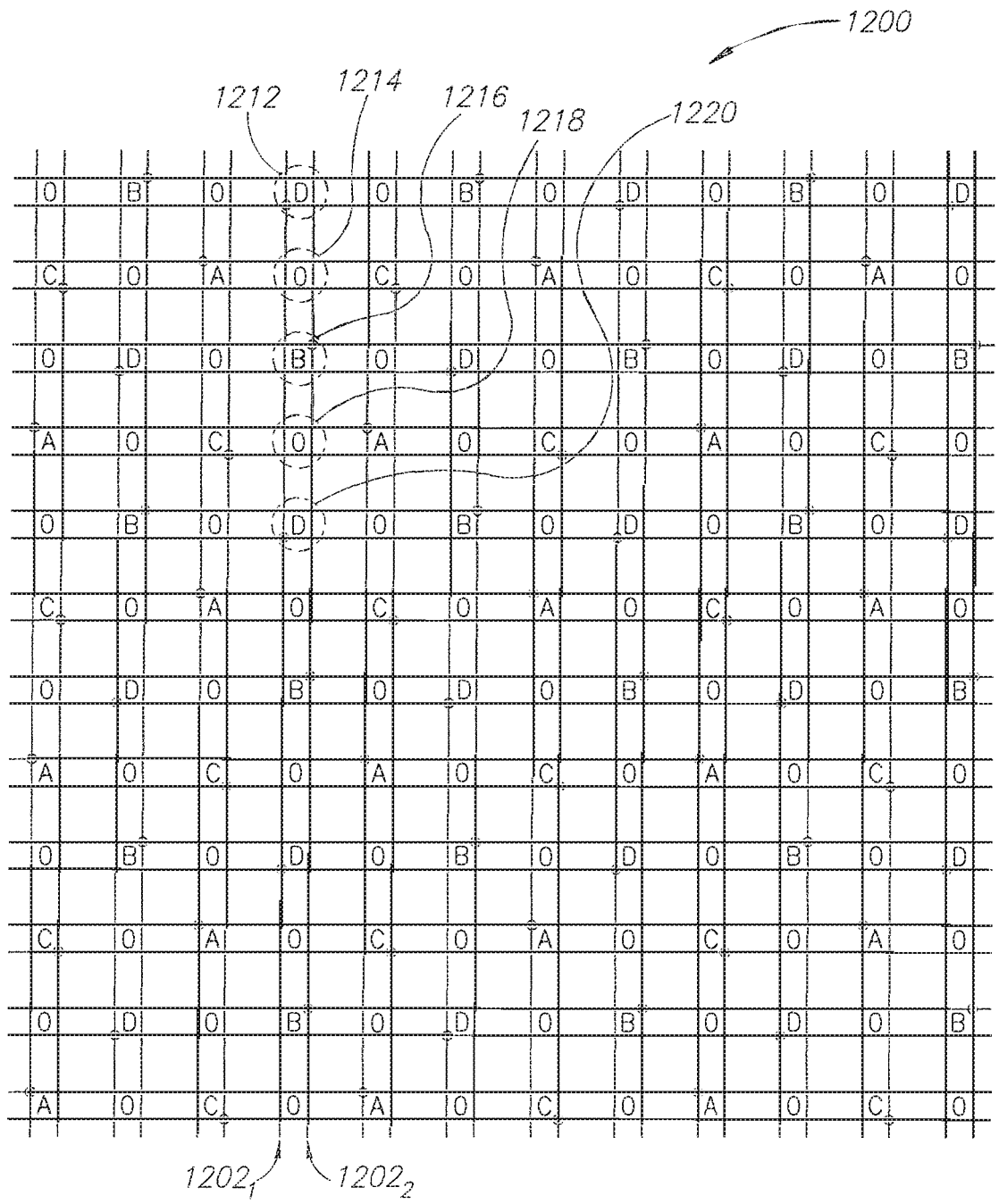

According to embodiments of the invention a net-work may be constructed using "twinned" (i.e., doubled) adjacent, substantially in loose parallel contact, singular monofila-ment threads. Reference is now made to FIGS. 12A-12C which are schematic illustrations of a tissue support struc-ture, generally referenced 1200 constructed and opera-tive in accordance with another embodiment of the disclosed technique. Tissue support structure 1200 includes twinned threads 1202₁ and 1202₂ which lie parallel to other twinned threads 1204₁ and 1204₂ and intersect twinned threads 1206₁ and 1206₂ and 1208₁ and 1208₂. Each of twinned threads 1202₁ and 1202₂, are in loose parallel contact with each other. Similarly twinned threads 1204₁ and 1204₂, twinned threads 1206₁ and 1206₂ and twinned threads 1208₁ and 1208₂ are also in loose parallel contact with each other. When a single thread intersects another single thread there is only one point of contact between them, referred to above as an "intersec-tion" for potential affixing. When twinned threads (e.g., 1202₁ and 1202₂) intersect other twinned threads (e.g., 1206₁ and 1206₂) there results a group of intersecting twinned threads, such as intersection group 1210, which includes four points of contact A, B, C and D, any one of which can potentially be affixed. It is noted that each of the contact points can be uniquely defined by the position thereof in the group of intersecting twinned threads, relative to the orienta-tion of the group to the overall matrix (e.g., D lower left corner of the group, B upper right corner).

FIG. 12B depicts an enlarged view of intersection group 1210 (FIG. 12A). When only one of the four contact points (e.g., A) is affixed, the three other contact points (B, C and D) remain free and mobile, resulting in an increase in the local compliance of the threads. Conversely, affixing more of the contact points of intersection group 1210 decreases the compliance (i.e., the mechanical response of the threads of the tissue support structure to a force applied thereon), which provides greater matrix stability. Thus, the extent of group fixation may be exploited to achieve an overall compliance and stability of the entire tissue support struc-ture, which may simultaneously reduce post-implantation pain and improve barrier or reinforcement functions.

FIG. 12C schematically illustrates how desired compli-ance may be achieved. In FIG. 12C, each intersection group (e.g., intersection groups 1212, 1214, 1216, 1218 and 1220) is labeled with one of the letter "A", "B", "C", or "D", corresponding to the affixed intersection position, as defined in FIG. 12B or with "O" when none of the intersection posi-tions in group is affixed. For each one of the single threads (e.g., 1202₁) of a twinned pair 1202₁ and 1202₂, the thread remains non-affixed for a segment of three intersec-tion groups. In the fourth intersection group, thread 1202₁ is affixed, as represented by a bold dot at position D. Accord-ingly, for any single thread, there is potential for mobility and compliance. A different thread (e.g., 1202₂) is affixed at a different intersection position (i.e., B) at the fourth inter-sec-tion group of thread 1202₂. The result is that every second group is affixed, albeit at just one of its four contact points. This increases the stability of tissue support structure 1200 as illustrated in FIG. 12C, while increasing the com-pliance of individual threads. This is depicted by twinned threads 1202₁ and 1202₂ and the groups they form with other twinned threads. In FIG. 12C, affixed intersections are depicted by a bold dot and their intersection position is indicated by the letter within each intersection group. A first group 1212 is affixed only at its intersection position D, the following group 1214 is not affixed at all (marked "O"). The next group 1216 is affixed only at its intersection group position B and the fourth group 1218 is not affixed. The sequence along this individual thread then begins again with group 1220. Affixing the threads as described above achieves a desired compliance in an orderly fashion, with the specific position of the affixed contact point (A, B, C, D) within each twinned intersection group being as equally spaced as possible across the network. Thus, no group ever occurs in near proximity to another group with identical affixed contact point. For example, a group with affixed 'upper left' (A) is surrounded by groups with either 'upper right' (B), 'lower right' (C) or 'lower left' (D) fixation, or by groups which are not affixed (0). Thus, groups in which the same contact point is affixed are at the largest possible distance from each other, thus simultaneously increasing compliance while maintaining stability.

In summary, a tissue support structure according to the disclosed technique employs a twinned pair of threads, which intersect other twinned pairs at intersecting groups such that there are at least four uniquely identifiable thread contact point positions in each group which can be selectively affixed to increase compliance and maintain stability.

Each set of twinned threads in tissue support struc-ture 1200 (FIGS. 12A and 12C), includes a pair of only two threads. However, each set may include three or more adja-cent threads. For example, each thread in a set of three adja-cent threads is affixed once every ninth intersection with other threads, such that each third intersection group includes at least one affixed contact point. As described above, such a tissue support structure may be designed such that intersec-tion groups in which the same intersection position is affixed are at the largest possible distance from each other. It is, however, noted that more than one inter-section position within a single intersection group may be simultaneously affixed. Thus, meshes can be designed with respective com-pliance and stability according to abdominal wall stresses.

The stability of such a network of compliant twinned threads is particularly relevant and advantageous for use in the abdominal wall where forces acting to either dis-perse or "bunch up" individual network threads (thus decreas-ing their barrier function) are resisted by the orderly arrange-ment of partially affixed complexes, as illustrated above. Nevertheless compliance, which contributes to the reduction in pain, is maintained. Such orderly partial affixing of the threads may be integrated into the network by automated or manual means as described. Affixing the threads randomly may achieve a similar overall stability/compliance ratio and may have manufacturing advantages.

It should be noted that when only single, non-twinned, threads are used, desired matrix compliance and thus matrix stability, can be achieved by simply altering the frequency of affixing of the single thread intersections. Twinned threads, tripled threads and the like, may be used in any of the embodiments described above.

As mentioned, a tissue support structure exhibiting the matrix configuration, affixed (e.g., molded) at all the inter-sections thereof, has less potential for thread compli-ance. However, since such matrices still incorporate uniquely wide spaces (e.g., 2 cm in diameter) inherent in the matrix configuration, even a minimal decrease in thread tautness, between the affixed intersections, can substantially increase compliance.

Figure 13A:
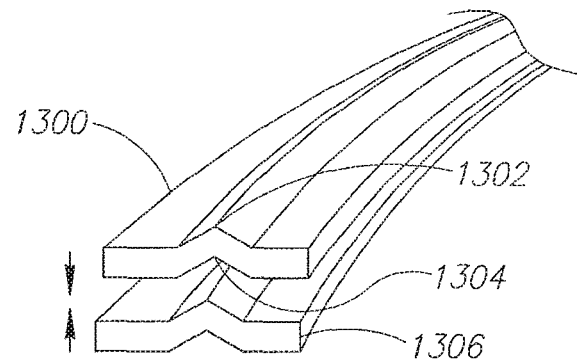
FIGS. 13A-13G, are schematic illustrations of cross-sections of various stabilizing perimeter structures, con-structed and operative in accordance with a further embodi-ment of the disclosed technique.
Figure 13B:
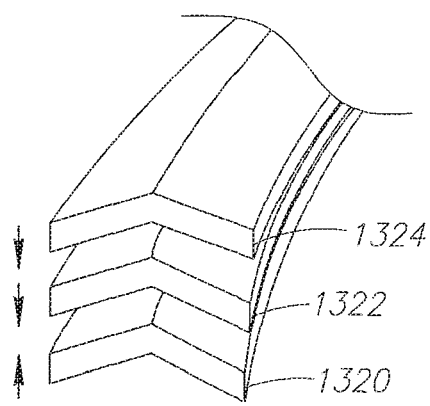

As mentioned above, in a tissue support structure exhib-iting the parallel lines configuration, a surgeon has the option of layering one tissue support structure on top of another at different angles during surgery. The final configu-ration having reinforcing or barrier functions is thus pro-duced during surgery. This may require coupling one stabi-lizing perimeter structure to another. Accordingly, the stabilizing perimeter structures of the disclosed technique are configured to enable the coupling of one perimeter structure to another to achieve a multilayered device. As described above in con-junction with FIGS, a circular or quadrilateral perim-eter structure is constructed of a frame whose cross-section has various shapes. Reference is now made to FIGS. 13A-13G, which are schematic illustrations of cross-sections of various stabilizing perimeter structures, constructed and operative in accordance with a further embodiment of the disclosed technique. With reference to FIG. 13A, a frame 1300 exhibiting a substantially rectan-gular cross-section, has an elevation or ridge 1302 at the center of the upper side thereto, with corresponding inden-tation 1304 of the under-side thereof, allowing stable cou-pling of a similar frame 1306 with frame 1300. With reference to FIG. 13B, the cross-section of each of frames 1320, 1322 and 1324 exhibit an inverted V-shape to allow the stable coupling of frames.

Figure 13C:
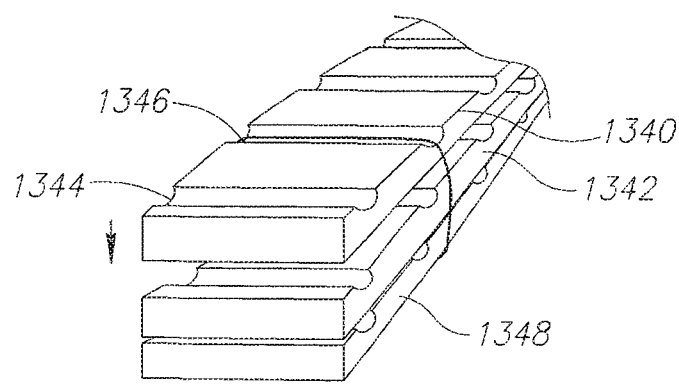

With Reference to FIG. 13C, small grooves such as groove 1344 engraved across the top of frame 1340 at prede-termined intervals. The small grooves such as groove 1344 are designed to hold a suture 1346 which passes around frames 1340, 1342 and 1348. The suture typically passes simultaneously through the underlying tissues and securely tightens into groove 1344, thus simultaneously securing the frames one to the other, and to the tissues.

Figure 13D:
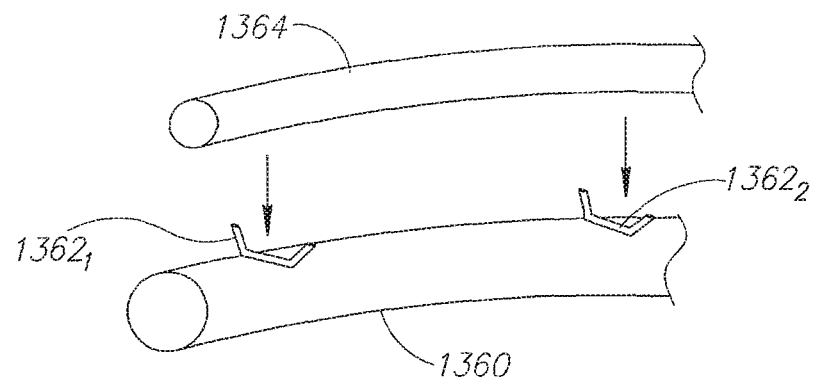

With reference to FIG. 13D a frame (i.e., a stabiliz-ing perimeter structure) 1360, which exhibits a circular cross-section, is manufactured with coupling elements such as clips 13621 and 13622. Another frame such as frame 1364 may be inserted into clips 13621 and 13622 thus coupling the two frames.

Figure 13E:
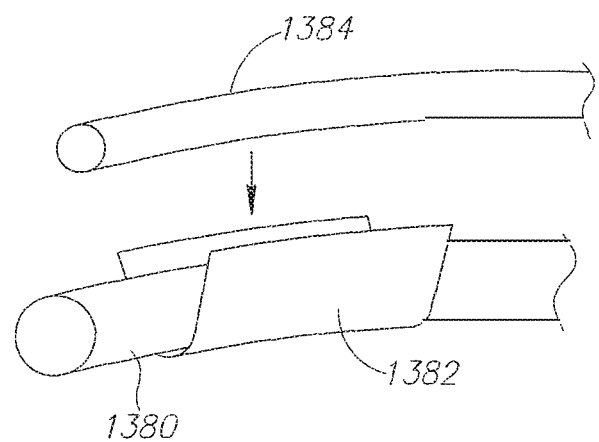

With reference to FIG. 13E a frame 1380, which exhibits a circular cross-section, is manufactured with a cou-pling element such as a housing 1382. Another frame, such as frame 1384 may be inserted into housing 1382 thus coupling the two frames. It is noted that coupling elements are not limited to frames which exhibit a circular cross-section. Such coupling elements may be manufactured with frames which exhibit other cross-sections such as those described above in conjunction with FIGS.

Figure 13F:
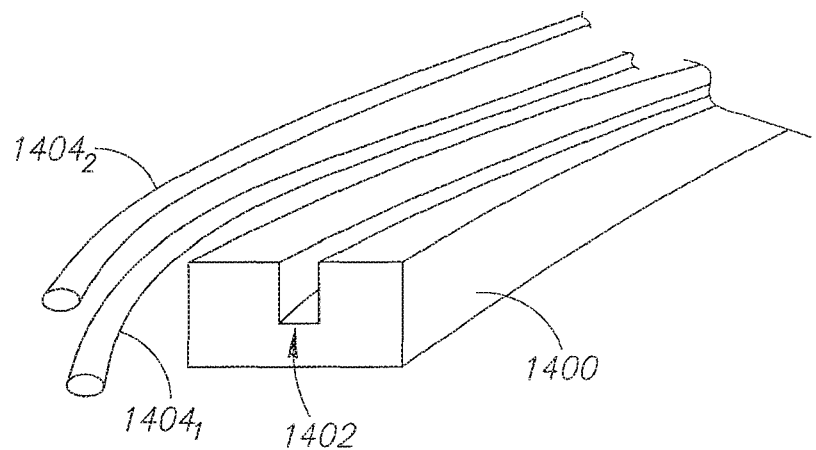
Figure 13G:
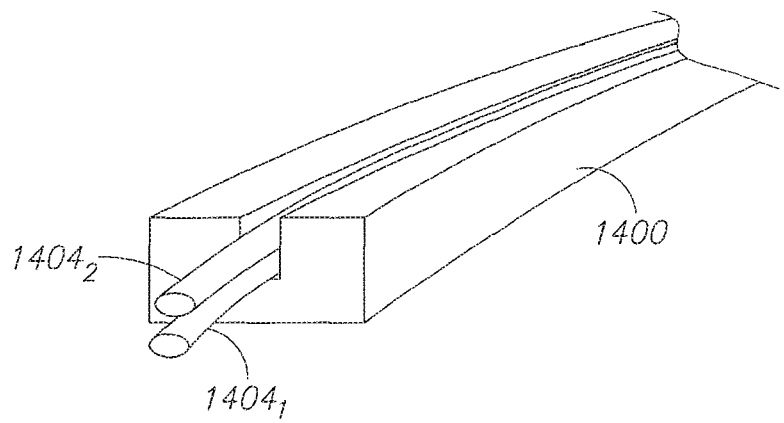

With reference to FIGS. 13F and 13G, frame 1400, exhibiting a generally rectangle-cross section, has a groove 1402 running longitudinally along the upper surface thereof. Other tissue support structures with respective stabilizing perimeter structures such as stabilizing perimeter structures 14041 and 14042, exhibiting a narrower cross-section than groove 1402, may be inserted securely into groove 1402, for example, one on top of the other as illustrated in FIG. 13F, and are thus layered on as illustrated in FIG. 13G.

According to the disclosed technique, using a sin-gular non-braided monofilament thread reduces the thread inter-section density (i.e., the number of thread intersections per 100 square centimeters) and increases the effective poros-ity (i.e., either existing spaces allowing for unimpeded tissue ingrowth or spaces created during the ingrowth of the tissue) relative to known in the art meshes. This results in substantially reducing the tissue reaction to the structure while main-taining the incorporability thereof. As mentioned above, the relatively high intersection density (e.g., 250,000 intersec-tions per 100 cm2) of woven or entangled braided monofila-ment threads and multifilament threads in known in the art fiber based meshes results in complicated tissue reactions (e.g., chronic pain and infection) in these known in the art meshes.

Tissue support structures according to the disclosed technique relate to networks exhibiting the same non-reactivity as known in the art smooth solid sheets, but, as opposed to known in the art smooth solid sheets, are also incorporable. Moreover, the tissue support structures according to disclosed technique provides an inert and permanent "scaffolding", around which normal healing processes occur to strengthen the abdominal wall. Furthermore, the nonreactive incorporable "scaffolding" can be manipulated to spatially extend normal healing processes, which is useful, for example, in the definitive closure of wide-open catastrophic abdomens.

It is noted that the tissue support structure according to the disclosed technique limits tissue reactions to an extent equivalent to a fully dissolved biologic mesh. However, as opposed to biological meshes, tissue support structures according to the disclosed technique are also permanent and thus can prevent hernia recurrence. It is also noted that the production cost of a tissue support structure according to the disclosed technique is currently lower than the production cost of a known in the art biological mesh. However, when necessary, biologic meshes, biological threads or absorbablecoatings may be incorporated into the tissue support struc-tures of the disclosed technique.

The non-braided monofilament threads of a tissue support structure according to the disclosed technique may also be coated by, or otherwise conjugated with drug delivery sys-tems and cell micro-carriers which have known skin-engineering applications (e.g., skin formation). Drugs (e.g., epi-dermal growth factors) and cells (e.g., keritanocytes and fibroblasts) with the ability to increase granulation and epi-thelialization can thus be used to increase skin formation across the area covered by the tissue support structure. Examples of relevant drug delivery systems are dextran-base hydrogels, nano-scaled poly (epsilon-caprolactone) gelatin fibrous scaffold, and injectable forms of silicon-resin particles. Examples of cell micro-carriers are dextran gelatin particles and plastic particles made of polyethylene or poly-styrene. As mentioned, stabilizing structures and the thread sections of a tissue support structure according to the dis-closed technique may be hollow or fenestrated, thus allowing their impregnation with the skin-engineering drugs or cells.

A desirable place to implant a tissue support struc-ture is on the highly accessible outer surface of the abdominal muscles (i.e., onlayplacement). This is precluded with known in the art meshes since, as described above, they may become infected in the onlay position. However, the tissue support structures according to the disclosed technique prevent chronic infection, allowing full utilization in the onlay posi-tion. Thus, tissue support structures according to the dis-closed technique may be applied during surgery, for example, for routine hernia prophylaxis. In summary, tissue support structures according to the disclosed technique provide a new incorporable and non-reactive solution for hernia repair.

Tissue support structures according to the disclosed tech-nique may similarly be used as non-reactive and incor-porable tissue implants in other medical procedures, for example, esophageal replacement, chest wall reconstruction, large area skin graft substrate, pelvic soft-tissue reconstruction (e.g., pelvic floor slings) and conduit reconstruction (e.g., intestinal and ureteral stomae) and management (e.g., treat-ment of prolapse), acetabular replacement and cement restric-tion in orthopedic surgery, as well as for abdominal wall reconstruction as described in detail herein above. For some uses, a smaller diameter mono filament nylon thread (e.g., less than 0.2 mm in diameter) may be employed to allow more closely arrayed threads or increased flexibility without losing non-reactivity and incorporability, as for example, to allow the matrix configuration to be rolled into a flexible cylindrical shape to provide a permanent artificial surface for esophageal replacement.

It will be appreciated by persons skilled in the art that the disclosed technique is not limited to what has been particularly shown and described hereinabove. Rather the scope of the disclosed technique is defined only by the claims, which follow.

Figure 14:
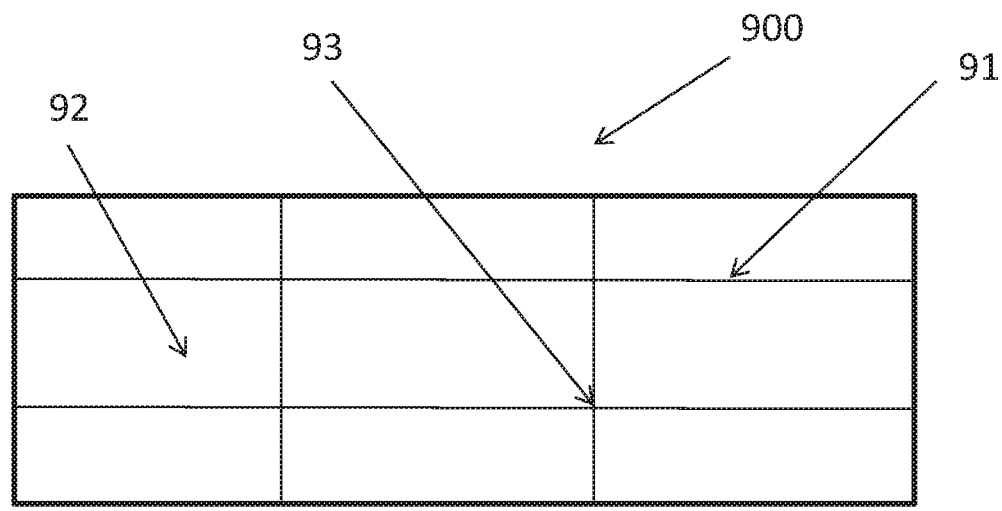
FIG. 14 illustrates the implantable areal device (900) that is formed by the thread sections (91) which define void spaces (92), and that includes intersections (93).

We may refer hereinafter and in the claims to the tissue support structure in general as an implantable areal device (900) for supporting abdominal wall tissue mechanically and by regeneration of muscle and fascial tissue. The implant-able areal device (900) is formed by a plurality of thread sections (91), which define a plurality of void spaces (92), wherein at least one of the void spaces is more than one-hundred square millimeters in area. The implantable areal device (900) is in fact designed to support and to enable regeneration of any kind of tissue and fascia, and we use the specific case of abdominal wall only for illustration. FIG. 14 illustrates the implantable areal device (900) that is formed by the thread sections (91) which define void spaces (92), and that includes intersections (93).

It is now understood that the purpose of the disclosed technique and device is to repair abdominal wall musculo-fascial defects by immediately providing stable mechanical support which is followed by functional support provided by musculofascial tissue regeneration. The disclosed technique and device overcome the disadvantages of the prior art by providing an implantable areal device for medical applications, for example for the treatment of hernias of the abdominal wall. The tissue support structure according to the disclosed technique is an implantable, non-reactive and regenerative structure preferably formed by an arrangement of permanent non-reactive singular monofilament thread sections which define a plurality of void spaces, from 100 square millimeters to 3000 square millimeters or even larger. As a consequence, the structure fulfills the two conditions which are necessary and sufficient for mechanical regeneration of skeletal muscle and fascia. Stabilization of the defective tissues is the first condition which must be met. The support structure stabilizes defective tissues by its structural arrangement of singular monofilaments, which when fixed to the defective tissues relatively immobilizes them, and reinforces or bridges the defective tissues to prevent re-herniation through them. The second condition which must be met for musculofascial regeneration is counter-intuitive, since it presumes that stabilization must be achieved contrary to the current paradigm which predicates collagen deposition and scar tissue formation, as these are both strong inhibitors of naturally-occurring musculofascial regeneration. Nevertheless, this is achieved by the disclosed device and technique through its wide open void spaces (92), each greater than 100 square millimeters. Such an area void of any inhibitory foreign body has been confirmed clinically to be the minimal area necessary for musculofascial regeneration to proceed to completion.

The final result is that the widely separated, flexible and non-infectable singular monofilaments are engulfed by volumetric amounts of regenerated functionalized musculofascial tissues possessing superlative strength. This is in stark contrast to the long standing paradigm in which the end result of mesh implantation is exuberant scar tissue formation. For example, as recently stated in the leading surgical journal, Annals of Surgery, "The efficacy of mesh repairs is based on strengthening weakened native tissue by scar tissue formation, formed by the inflammatory response induced by mesh material" [pub ahead of print, January, 2018]. Moreover, it is well known that the encapsulating scar tissue is the chief source of the prior art's common and serious clinical complications, and since scar tissue formation is entirely absent in the disclosed technique, where instead there is newly regenerated functioning musculofascial tissues, the disclosed technique provides a unique solution for treating abdominal wall hernias both effectively and without complications.

According to the above explanations and those to follow, we can summarize the invention in the manner described below:

The implantable areal device (900) is designed for supporting defective tissue mechanically and by regeneration of muscle and fascial tissue. The implantable areal device is formed by a plurality of thread sections (91), wherein the thread sections define a plurality of void spaces (92), wherein at least one of said void spaces is more than one-hundred square millimeters in area. The device may include two, three, four, five or more void spaces that are more than one-hundred square millimeters in area. The implantable areal device (900) may be designed in a way that at least 80 percent of its area comprises void spaces each more than one-hundred square millimeters in area. It is possible that the implantable areal device (900) will comprise at least one void space more than four-hundred square millimeters, or even more than one-thousand square millimeters, in area.

It is possible and even preferable that the implantable areal device (900) will be formed by plurality of singular monofilament thread sections (91) and that said implantable areal device includes less than 121 thread intersections per one-hundred square centimeters, and for this matter, thread intersection is defined as a crossing of two of said thread sections.

It is also possible that the implantable areal device (900) may be formed by a plurality of thread sections (91) which are selected from the group consisting of braided monofilaments, knitted monofilaments, knotted monofilaments, singular multifilaments, braided multifilaments, knitted multifilaments and knotted rnultifilaments, and comprises less than 10,000 intersections per one-hundred square centimeters, intersection being defined as crossing of two said thread sections and as crossing of two filaments of at least one thread section. It is also possible that the cross-sectional diameter of the thread sections may be from 0.02 millimeters to 10 millimeters, and that thread section cross-sectional shape is at least one of circle, ellipse, square and rectangle.

It is also possible that the singular monofilaments are produced by, and at least one intersection of singular monofilaments is fixated by, at least one of injection molding, fusing, adhering, sintering, extruding, 3-D printing and laser cutting. It is also possible that the shape of at least one void space more than one-hundred square millimeters in area is one of square, rectangular, quadrilateral, convex polygonal, concave polygonal, circular, oblong and curved. It is also possible that at least one filament comprises at least one of synthetic and natural non-absorbable material of at least one of plastic, metal, carbon, spider web and silk. It is also possible that at least one filament comprises at least one of synthetic and biological absorbable materials including at least one of polyglycolic acid, polyglactin 910, poly-4-hydroxybutyrate and decelluraized extracellular matrix of at least one of porcine, bovine, ovine and human origin.

Figure 15:
FIG. 15 illustrates a thread section of Z-shape.
Figure 16:
FIG. 16 illustrates a thread section of S-shape.
Figure 17:
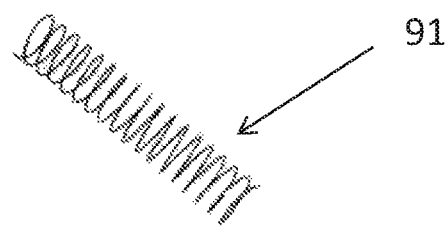
FIG. 17 illustrates a thread section of spiral-shape.

The implantable areal device may contain an eluting drug whose effect is antibacterial, stimulatory for tissue regenerative precursor cells, or stimulatory for regenerative biological signals, that are needed following implantation for tissue regeneration. The implantable areal device may include at least one thread section that comprises at least one of Z-shaped, S-shaped or spiral-shaped elastic segment allowing said segment to stretch as an elastic spring. The implantable areal device may include threads sections that comprise at least one auxetic structure having a shape such as re-entrant honeycomb or cut missing rib, or wherein at least one of said thread sections comprises an auxetic helix. FIG. 15 illustrates a thread section of Z-shape, FIG. 16 illustrates a thread section of S-shape, and FIG. 17 illustrates a thread section of spiral-shape.

The present invention refers also to methods that use the device (900) for several goals. First, the invention refers to a method for supporting defective musculofacial tissue mechanically and by in-situ tissue engineering, that is based on the following: providing the implantable areal device (900), and fixating it by open surgical techniques to defective musculofascial tissue. In this method the fixation immediately provides mechanical support of the tissue, and subsequently provides physiological repair by allowing regenerative precursor cells to infiltrate freely into the void spaces and to proliferate therein, leading to regeneration of volumetric amounts of functionalized musculofascial tissue. Second, this method may further comprise the following: providing the implantable areal device wherein the thread sections are singular monofilaments, and the fixation of the implantable areal device to the musculofacial tissue is done intraperitoneally via laparoscopy. In this method, the implantable areal device immediately provides mechanical support of the tissue and subsequently allows physiological repair by enabling regeneration of functionalized musculofascial tissues, while simultaneously reducing the occurrence of postoperative intraperitoneal visceral adhesions, due to said device being comprised solely of non-adhesiogenic said monofilament thread sections and said void spaces. Third, the first method, wherein the defective muscle and fascial tissues are also contaminated or grossly infected, further comprises: providing the implantable areal device wherein the thread sections are singular monofilaments, whereby the implantable areal device immediately provides mechanical support of the tissues, and subsequently provides physiological support by allowing regeneration of volumetric amounts of functional musculofascial tissues, while simultaneously enabling normal resolution of infection due to said device being comprised solely of non-infectable said singular monofilament thread sections and said void spaces. Fourth, the third method for supporting defective and contaminated or grossly infected musculofascial tissues mechanically and by in situ tissue engineering, wherein the contamination or gross infection is a result of damage-control surgery based on open abdomen cavity, which further comprises the followings: applying the implantable areal device to the open abdominal cavity, whereby the device's non-infectable and non-adhesiogenic nature provides protective covering of exposed abdominal contents while reducing surgical complications such as chronic wound infection and entrocutaneous fistula, or facilitates early skin grafting or definitive musculofascial closure of the abdominal wall.

Fifth, a method of in-situ tissue engineering for surgical reconstruction of volumetric muscle loss using autologous tissues, which is based on the following: (a) providing the implantable areal device, (b) fixating the implantable areal device to a donor site comprising initially normal musculofacial tissue which has been prepared by preliminary intentional injury thereby causing musculofasical tissues to regenerate in and around said device following its fixation to said tissue; (c) excising in toto from the donor site the implanted areal device together with newly formed musculofascial tissue within and surrounding the areal device, and (d) transplanting en masse the implanted areal device together with the newly formed musculofascial tissue within and surrounding the areal device, to autologous recipient site of defective musculofascial tissue. At the recipient site, the transplanted regenerated autologous musculofascial tissue re-vascularizes and continues to further regenerate, producing volumetric amounts of functionalized musculofascial tissue in-situ.

Sixth, a method for augmenting strength of closed incision and hernia repair of abdominal wall, that comprises the following: (a) providing two implantable areal devices; (b) placing these devices as a sandwich on both sides of abdominal wall tissue to be supported, and (c) fixating the devices together with the abdominal wall tissue in between by through-and-through sutures or other fixation method. This method prevents re-opening of the closed incision and of the hernia repair by preventing displacement of any portion of the sandwiched abdominal wall relative to the two fixated devices. FIG. 18 illustrates schematically two implantable areal devices (900) that are placed as a sandwich on both sides (941) (942) of a tissue (94).

Seventh, a method for treating defective musculofascial tissue, which comprises the following: (a) providing the implantable areal device combined with a layer of biological or synthetic absorbable material that fills the void spaces, and (b) fixating the device combined with the absorbable layer to defective musculofascial tissue. By this method, the absorbable layer prevents tissue herniation through the void spaces between the thread sections, until the layer is absorbed and replaced by regenerated musculofascial tissue.

What is claimed is:

1. An implantable areal device for supporting defective musculofascial tissue mechanically and by regeneration of muscle and fascial tissue; wherein said implantable areal device is formed by a plurality of thread sections; wherein said thread sections define a plurality of void spaces; wherein at least one of said void spaces is more than one-hundred square millimeters in area; wherein said plurality of thread sections are singular monofilament, and wherein said implantable areal device comprises less than 121 thread intersections per one-hundred square centimeters, thread intersection being defined as crossing of two of said thread sections.

2. The implantable areal device for supporting defective musculofascial tissue mechanically and by regeneration of muscle and fascial tissue according to claim 1, wherein at least one of said thread sections comprises at least one of Z-shaped, S-shaped or spiral-shaped elastic segment allowing said segment to stretch as an elastic spring.

3. The implantable areal device for supporting defective musculofascial tissue mechanically and by regeneration of muscle and fascial tissue according to claim 1, wherein said threads sections comprise at least one auxetic structure having a shape such as re-entrant honeycomb or cut missing rib, or wherein at least one of said thread sections comprises an auxetic helix.

4. An implantable areal device for supporting defective musculofascial tissue mechanically and by regeneration of muscle and fascial tissue; wherein said implantable areal device is formed by a plurality of thread sections; wherein said thread sections define a plurality of void spaces; wherein at least one of said void spaces is more than one-hundred square millimeters in area; wherein said plurality of thread sections are selected from the group consisting of braided monofilaments, knitted monofilaments, knotted monofilaments, singular multifilaments, braided multifilaments, knitted multifilaments and knotted multifilaments; wherein said implantable areal device comprises less than 10,000 intersections per one-hundred square centimeters, intersection being defined as crossing of two said thread sections and as crossing of two filaments of at least one thread section.

5. An implantable areal device for supporting defective musculofascial tissue mechanically and by regeneration of muscle and fascial tissue according to claim 4, wherein at least one of said thread sections comprises at least one of Z-shaped, S-shaped or spiral-shaped elastic segment allowing said segment to stretch as an elastic spring.

6. An implantable areal device for supporting defective musculofascial tissue mechanically and by regeneration of muscle and fascial tissue according to claim 4, wherein said threads sections comprise at least one auxetic structure having a shape such as re-entrant honeycomb or cut missing rib, or wherein at least one of said thread sections comprises art auxetic helix.

7. A method for supporting defective musculofacial tissue mechanically and by in-situ tissue engineering, comprising:
 (a) providing an implantable areal device that is designed for supporting defective musculofascial tissue mechanically and by regeneration of muscle and fascial tissue, wherein the implantable areal device is formed by a plurality of thread sections, wherein said thread sections define a plurality of void spaces, wherein at least one of said void spaces is more than one-hundred square millimeters in area, wherein said plurality of threads sections are singular monofilament, wherein said implantable areal device comprises less than 121 thread intersections per one-hundred square centimeters, thread intersection being defined as crossing of two of said thread sections, and
 (b) fixating by open surgical techniques said implantable areal device to defective musculofascial tissue;
 whereby said fixation immediately provides mechanical support of said tissue, and subsequently provides physiological repair by allowing regenerative precursor cells to infiltrate freely into said void spaces and to proliferate therein, leading to regeneration of volumetric amounts of functionalized musculofascial tissue.

8. A method for supporting defective musculofacial tissue mechanically and by in-situ tissue engineering according to claim 7, further comprises:
 (a) providing said implantable areal device;
 (b) fixating said implantable areal device wherein said fixation to musculofacial tissue is done intraperitoneally via laparoscopy,
 whereby said implantable areal device immediately provides mechanical support of said tissue and subsequently allows physiological repair by enabling regeneration of functionalized musculofascial tissues, while simultaneously reducing the occurrence of postoperative intraperitoneal visceral adhesions, due to said device being comprised solely of non-adhesiogenic said monofilament thread sections and said void spaces.

9. The method for supporting defective musculofascial tissues mechanically and by in-situ tissue engineering according to claim 7, wherein said defective muscle and fascial tissues are also contaminated or grossly infected, further comprising:
(a) providing said implantable areal device;
whereby said implantable areal device immediately provides mechanical support of said tissues, and subsequently provides physiological support by allowing regeneration of volumetric amounts of functional musculofascial tissues, while simultaneously enabling normal resolution of infection due to said device being comprised solely of non-infectable said singular monofilament thread sections and said void spaces.

10. A method for supporting defective and contaminated or grossly infected musculofascial tissues mechanically and by in situ tissue engineering according to claim 9, wherein said contamination or gross infection is a result of damage-control surgery based on open abdomen cavity, further comprising:
(a) applying said implantable areal device to said open abdominal cavity;
whereby said device's non-infectable and non-adhesiogenic nature provide protective covering of exposed abdominal contents while reducing surgical complications such as chronic wound infection and entrocutaneous fistula, or allow early skin grafting or definitive musculofascial closure of the abdominal wall.

11. A method for treating defective musculofascial tissue, comprising:
(a) providing an implantable areal device that is designed to provide immediate mechanical support for defective musculofascial tissue and subsequent physiological repair by regeneration of said tissue, wherein the implantable areal device is formed by a plurality of thread sections, wherein said thread sections define a plurality of void spaces, wherein at least one of said void spaces is more than one-hundred square millimeters in area; wherein said plurality of threads sections are singular monofilament, and wherein said implantable areal device comprises less than 121 thread intersections per one-hundred square centimeters, thread intersection being defined as crossing of two of said thread sections; wherein said device is combined with a layer of biological or synthetic absorbable material that fills said void spaces, and
(b) fixating said device combined with said absorbable layer to said defective musculofascial tissue;
whereby said absorbable layer prevents tissue herniation through said void spaces, until said layer is absorbed and replaced by regenerated musculofascial tissue.

12. A method for supporting defective musculofacial tissue mechanically and by in-situ tissue engineering, comprising:
(a) providing an implantable areal device that is designed for supporting defective musculofascial tissue mechanically and by regeneration of muscle and fascial tissue, wherein the implantable areal device is formed by a plurality of thread sections, wherein said thread sections define a plurality of void spaces, wherein at least one of said void spaces is more than one-hundred square millimeters in area, wherein said plurality of thread sections are selected from the group consisting of braided monofilaments, knitted monofilaments, knotted monofilaments, singular multifilaments, braided multifilaments, knitted multifilaments and knotted multifilaments; wherein said implantable areal device comprises less than 10,000 intersections per one-hundred square centimeters, intersection being defined as crossing of two said thread sections and as crossing of two filaments of at least one thread section, and
(b) fixating by open surgical techniques said implantable areal device to defective musculofascial tissue;
whereby said fixation immediately provides mechanical support of said tissue, and subsequently provides physiological repair by allowing regenerative precursor cells to infiltrate freely into said void spaces and to proliferate therein, leading to regeneration of volumetric amounts of functionalized musculofascial tissue.

* * * * *